(12) United States Patent
Schlueter et al.

(10) Patent No.: US 10,408,747 B2
(45) Date of Patent: Sep. 10, 2019

(54) GAS INLET SYSTEM FOR ISOTOPE RATIO SPECTROMETER

(71) Applicant: Thermo Fisher Scientific (Bremen) GmbH, Bremen (DE)

(72) Inventors: Hans-Juergen Schlueter, Bremen (DE); Johannes Schwieters, Ganderkesee (DE); Eric Wapelhorst, Bremen (DE); Michael Krummen, Bad Zwischenahn (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 0 days.

(21) Appl. No.: 16/163,436

(22) Filed: Oct. 17, 2018

(65) Prior Publication Data

US 2019/0086328 A1    Mar. 21, 2019

Related U.S. Application Data

(63) Continuation of application No. 15/034,174, filed as application No. PCT/EP2014/074205 on Nov. 10, 2014, now Pat. No. 10,151,690.

(30) Foreign Application Priority Data

Nov. 8, 2013   (GB) .................................. 1319766.0

(51) Int. Cl.
*H01J 49/00*  (2006.01)
*G01N 21/3504*  (2014.01)
(Continued)

(52) U.S. Cl.
CPC ......... *G01N 21/3504* (2013.01); *G01N 21/11* (2013.01); *G01N 30/7206* (2013.01);
(Continued)

(58) Field of Classification Search
CPC .. G01N 21/3504; G01N 21/31; H01J 49/0422
(Continued)

(56) References Cited

U.S. PATENT DOCUMENTS 5,644,130 A * 7/1997 Raatz .................. H01J 49/0422
                                                    250/288
5,976,890 A    11/1999 Gehre et al.
(Continued)

FOREIGN PATENT DOCUMENTS

CN       1253660 A      5/2000
CN     101609075       12/2009
(Continued)

OTHER PUBLICATIONS

Benson, et al., "Forensic applications of isotope ratio mass spectrometry—A review", Forensic Science International 157 (2006), pp. 1-22.
Brenna, et al., "High-precision continuous-flow isotope ratio mass spectrometry", Mass Spectrometry Reviews 16(5), 1997, pp. 227-258.

*Primary Examiner* — Michael Maskell
(74) *Attorney, Agent, or Firm* — David A. Schell

(57) ABSTRACT

A gas inlet system for an isotope ratio spectrometer and a method for coupling analyte gas to an isotope ratio spectrometer are disclosed. A variable volume reservoir is located between a supply of analyte gas and a spectrometer. The reservoir's internal volume is controllably adjusted at a pre-determined rate to generate a defined flow of analyte gas or mixture to or from the reservoir. Analyte gas and carrier gas are taken up by the reservoir on increasing the reservoir's internal volume and then expelled from the reservoir to the spectrometer on decreasing the reservoir's internal volume. An open split can be used together with the reservoir to facilitate splitting away and hence dilution of analyte
(Continued)

within the reservoir. A method for cleaning the gas inlet system is provided, which involves flushing the system with carrier gas.

22 Claims, 16 Drawing Sheets

(51) Int. Cl.
   *H01J 49/04* (2006.01)
   *G01N 21/11* (2006.01)
   *G01N 30/72* (2006.01)
   *G01N 30/84* (2006.01)
   *G01N 21/31* (2006.01)

(52) U.S. Cl.
   CPC .......... *G01N 30/84* (2013.01); *H01J 49/0422* (2013.01); *G01N 21/31* (2013.01); *G01N 2030/8411* (2013.01)

(58) Field of Classification Search
   USPC ........................................ 250/281, 282, 288
   See application file for complete search history.

(56) References Cited

U.S. PATENT DOCUMENTS

| | | | |
|---|---|---|---|
| 2003/0218131 A1* | 11/2003 | Fujita | G01N 1/22 250/288 |
| 2007/0274845 A1 | 11/2007 | Ruprecht et al. | |
| 2009/0159795 A1* | 6/2009 | Hatscher | H01J 49/0404 250/288 |
| 2010/0198736 A1* | 8/2010 | Marino | G01N 21/3504 705/308 |

FOREIGN PATENT DOCUMENTS

| | | |
|---|---|---|
| CN | 101936964 A | 1/2011 |
| CN | 102253136 A | 11/2011 |
| CN | 102405404 A | 4/2012 |
| CN | 102770759 A | 11/2012 |
| JP | 11083851 A | 3/1999 |
| JP | 2009-222613 A | 10/2009 |
| JP | 2009222613 A * | 10/2009 |
| WO | 2006/014555 A1 | 2/2006 |
| WO | 2010/088657 A2 | 8/2010 |

* cited by examiner

GAS INLET SYSTEM FOR ISOTOPE RATIO SPECTROMETER

CROSS-REFERENCE TO RELATED APPLICATIONS

The present application is a continuation under 35 U.S.C. § 120 and claims the priority benefit of co-pending U.S. patent application Ser. No. 15/034,174, filed May 3, 2016, which is a National Stage application under 35 U.S.C. § 371 of PCT Application No. PCT/EP2014/074205, filed Nov. 10, 2014. The disclosures of each of the foregoing applications are incorporated herein by reference.

FIELD OF THE INVENTION

This invention relates to a gas inlet system for an isotope ratio spectrometer such as an isotope ratio optical spectrometer (IROS) or an isotope ratio mass spectrometer (IRMS). The invention also relates to a method of coupling an analyte gas to an isotope ratio spectrometer.

BACKGROUND OF THE INVENTION

Isotope ratio analysis is used to measure the relative abundance of isotopes (isotope ratio) in a gaseous sample for example, the stable isotopic composition of oxygen and carbon ($^{18}O/^{16}O$ and $^{13}C/^{12}C$) is an important proxy indicator of paleoenvironmental changes recorded in carbonate minerals deposited for example, as marine sediments.

Isotope ratio mass spectrometry (IRMS) is a well-established technique for such analysis. IRMS offers relatively high throughput (several minutes of analysis time per sample) as well as high precision isotope measurements. However high precision is accomplished at the expense of flexibility; IRMS instruments accept analytes in the form of a relatively limited number of gases which must be isotopically representative of the original sample. One of the challenges in IRMS is to ensure that fractionation (i.e., a shift in the relative quantities of isotopes between the original sample analyte and the mass spectrometer) is minimized or prevented.

The two most common types of IRMS instruments are continuous flow and dual inlet. In dual inlet IRMS, purified gas obtained from a sample is alternated rapidly with a standard gas of known isotopic composition by means of a system of valves, so that a number of comparison measurements are made of both gases. In continuous flow IRMS, sample preparation occurs immediately before introduction to the IRMS, and the purified gas produced by the sample is measured just once. The standard gas may be measured before and after the sample, or after a series of sample measurements.

Whilst continuous flow IRMS instruments can achieve higher sample throughput and are more convenient to use than dual inlet instruments, the yielded data are of lower precision. A general review of IRMS and gas inlet systems for these may be found in Brenna et al, Mass Spectrometry Reviews, 1997, 16, p. 227-258.

IRMS is not, however, without disadvantages. It is not compatible with condensable gases or a sticky molecule such as water. If a mixture of gases is applied to the analyser, there is the danger of interferences by reactions within the ion source. Thus, generally, chemical preparation of the sample is necessary to transfer the isotope of interest to a molecule that is more easily analyzed, and to separate the sample from other gas molecules. Typically, though, the required steps of chemical conversion are time consuming, and may compromise overall accuracy and throughput. Moreover, in general terms, IRMS instruments tend to be expensive, voluminous, heavy, confined to a laboratory, and usually in need of a skilled operator.

Isotope ratio optical (usually infrared) spectrometry (IROS) is a more recently developed technique for isotope ratio analysis. Here, photo absorption by $H_2O$ molecules is measured and the isotopologies of $H_2O$ are calculated by spectroscopy. IROS has a number of benefits over IRMS, such as ease of use, cost and potential field portability. It also permits direct analysis of water, where IRMS requires initial conversion e.g. to $H_2$ or $CO_2$, or equilibration with $CO_2$, followed by analysis in gaseous form.

Relative to IRMS however, IROS typically offers a smaller dynamic range, poorer linearity, a larger measurement cell volume and pressure, such that more sample is required, and a higher pressure in the analyte cell.

Nevertheless, the gas load of an IR spectrometer may be very high. Thus, dilution of the sample to a relatively low concentration is often not a disadvantage. Indeed, given the limited dynamic range of an IROS instrument, significant dilution of the sample might be mandatory. The use of dry air as a carrier gas in IROS presents a further challenge relative to IRMS (where, typically, Helium is used as a carrier gas instead). The diffusion coefficient of $CO_2$ in air is 0.16 cm$^2$/sec, compared with a diffusion coefficient of about 0.7 cm$^2$/sec for $CO_2$ in Helium. Thus $CO_2$ mixes much more slowly (by a factor greater than 4) in an IROS instrument than in an IRMS device, such that, in an IROS instrument, mixing is a more challenging issue.

For the sample quantities required for infrared laser spectroscopy, the major part of the substance has to be transferred into the laser cell, for example by the use of a carrier gas. However, the transfer of the substance into the laser cell without fractionation (i.e. modification of the isotope signature) is demanding. In IRMS, fractionation can be avoided either by transferring only a small part of the substance, thus not disturbing the chemical equilibrium, or transferring (and measuring) substantially the whole sample. Different parts of the transferred sample may have different isotope signatures but the whole time dependent peak is used, and differences in isotope fractionation cancel one another out during integration. The same principle applies even if, a constant fraction of the sample is split away, along as that fraction is time constant, that is, the proportion of sample which is split away remains constant over the measurement period.

Unfortunately, neither principle is possible for IROS. It is not possible to transfer only a small part of the substance for IROS because most or all of the total substance is required for analysis. Likewise transferring the whole sample and relying upon integration of the whole time dependent peak is not possible for IROS either. The signal in the laser cell has to remain as constant as possible. A conventional "peak shaped" transient signal typically has a relatively small start and end part and these cannot be evaluated. These initial and final parts of the transient signal often differ in isotope distribution from the rest and it is therefore necessary to have these integrated into the whole sample result.

When the majority of the sample is transferred out of the closed volume by a carrier gas, diffusion occurs at the boundary carrier gas/analyte, which is what leads to fractionation. FIG. 1 shows an example of such fractionation: on the vertical axis, the isotope ratio is plotted in the form of a "delta" value, whilst the horizontal axis represents time. The left hand plot in FIG. 1 represents experimentally obtained data, whilst the right hand plot exhibits a theoretical calculation. In each case, fractionation is clearly visible.

Against this background, the present invention seeks to provide a gas inlet system for an isotope ratio spectrometer that allows an improved supply of analyte gas to the spectrometric analyzer. Although the present invention seeks in particular to address at least some of the challenges presented by an IROS instrument, it is nevertheless also concerned with improving the manner of supply of analyte gas to an IRMS device as well.

SUMMARY OF THE INVENTION

According to a first aspect of the present invention, there is provided a gas inlet supply for an isotope ratio spectrometer, in accordance with claim 1.

The invention also extends to the combination of such a gas inlet supply with an optical spectrometer such as an infrared spectrometer, or with a mass spectrometer.

According to a further aspect of the present invention, there is provided a method of coupling an analyte gas to an Isotope Ratio Spectrometer as set out in claim 42.

The gas inlet supply and method of the invention employ an intermediate reservoir of variable volume, i.e. located intermediate between the supply of analyte gas and the spectrometer. A constant decrease of the reservoir volume can be used to generate a constant flow of gas to the spectrometer. This permits a wide variety of analyte gas sources (e.g. vial, bag, syringe, sampling tube, gas chromatograph, TOC analyzer, laser desorption, combustion or ablation cells, and so forth) to be coupled to the spectrometer via the variable volume reservoir, so that, for example, a constant flow and/or pressure of gas to the spectrometer can be achieved, mixing of the analyte gas with a carrier can be improved, dilution of the analyte by a carrier can be carried out in a controlled and quantifiable manner, analyte concentration can be determined, and so forth. By locating the variable volume reservoir between the analyte source and the spectrometer, it is also possible, in preferred embodiments, to buffer a pulsed analyte supply in the reservoir and then deliver a constant or quasi-constant flow of analyte from the reservoir to the spectrometer.

As described in more detail below, the gas inlet supply and method of the invention preferably employ an open split. In this way, the gas inlet system preferably operates at or close to atmospheric pressure. The reservoir of variable volume is preferably fluidly coupled to the open split. The variable volume reservoir and open split can be used together to adjust the gas flow, so that a signal intensity from the analyte is in the optimum measurement range of the spectrometer and that it can be matched with optional reference gas pulses.

These advantages are especially useful in the case of an isotope ratio optical spectrometer. In another aspect of the present invention, there is provided a method of cleaning a gas inlet system for an isotope ratio mass spectrometer comprising the steps of: filling a reservoir in the gas inlet system with a carrier gas, and expelling the carrier gas from the reservoir to the isotope ratio mass spectrometer. Preferably, the carrier gas is expelled to the isotope ratio mass spectrometer via one or more gas supply lines. Preferably the reservoir is a variable volume reservoir and the carrier gas fills it by expanding the volume thereof so as to draw the carrier gas into the reservoir.

Preferably the carrier gas is expelled by compressing the variable volume reservoir.

Further advantages and preferred arrangements will become apparent upon review of the following description and drawings, and from the accompanying claims.

BRIEF DESCRIPTION OF THE DRAWINGS

The invention may be put into practice in a number of ways, some of which will now be described by way of example only and with reference to the accompanying drawings in which.

DETAILED DESCRIPTION OF A PREFERRED EMBODIMENT

Figure 1:
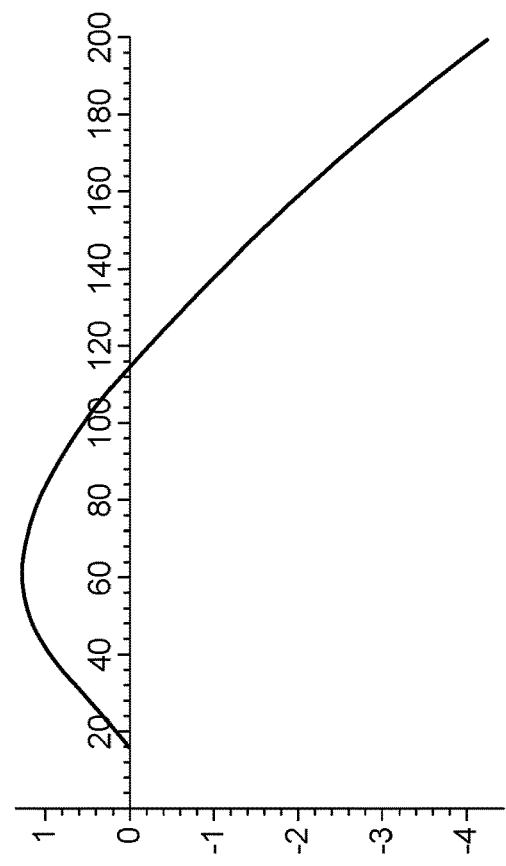
FIG. 1 shows a plot of isotope ratio against time illustrating fractionation in a prior art IROS device.
Figure 1:
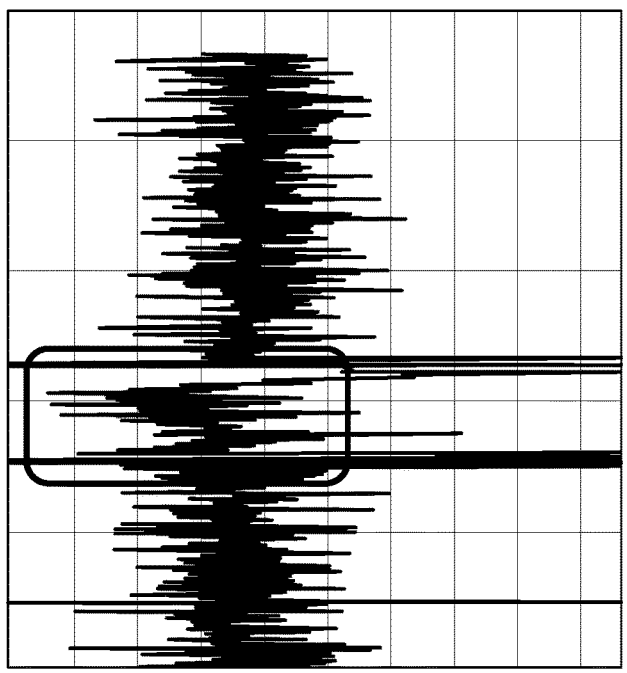
Figure 2:
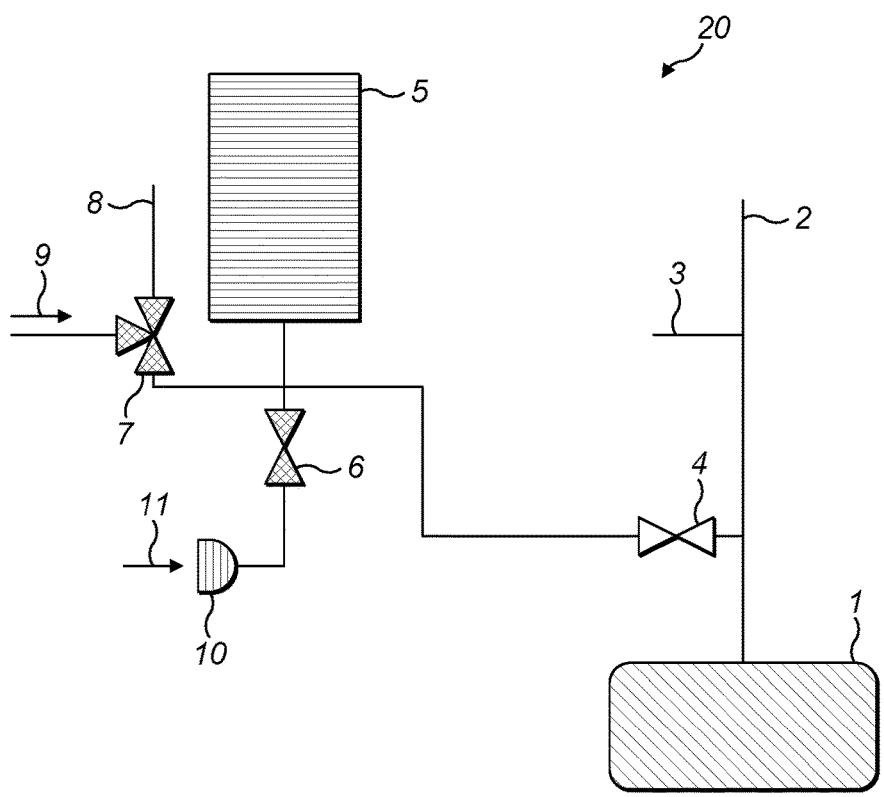
FIG. 2 shows a first embodiment of a gas inlet supply for a spectrometer exemplifying the present invention, and including a variable volume reservoir.

FIG. 2 shows the first embodiment of a gas inlet system 20 for an isotope ratio spectrometer, exemplifying the present invention. In general terms, and by way of introduction, the gas inlet system 20 comprises a variable volume reservoir 5 which is selectively connectible via gas supply lines and first and second supply valves 7,6 respectively to one or more sources of analyte gas 9,11 the variable volume reservoir 5 is also selectively connectible via an analyzer valve 4 to an isotope ratio analyzer 1. The isotope ratio analyzer 1 is, in preference, an optical/infrared analyzer (i.e. spectrometer) but might equally be a mass spectrometer.

The isotope ratio analyzer 1 is also supplied with carrier gas from a carrier gas supply 2, along a carrier gas supply line. At an arbitrary point along the carrier gas supply line is located an open split 3. The first supply valve 7 is also selectively connectable to a second open split 8.

Open splits are a well-known solution for gas flow management. In general terms, open splits comprise a region, e.g. for mixing gases, open to the atmosphere. Gases to be analyzed emerge from a line (in the case of FIG. 2, either off the carrier gas supply line between the carrier gas supply 2 and the analyzer 1, or via the first supply valve 7) into a mixing region. Though a large proportion of the gases is lost to atmosphere as excess, a small amount is transferred to a further line (not shown in FIG. 2). Thus, an open split can vent gas flow in excess of that which may be accepted by the isotope ratio analyzer.

An example of an open split design for isotope ratio mass spectrometry is shown in U.S. Pat. No. 5,424,539. A similar design is described in U.S. Pat. No. 5,661,038. Other examples may be seen in U.S. Pat. No. 7,928,369 and WO-A-2007/112,876. Gas inlet systems configured for auto dilution of samples using an open split are also known in the form of the Thermo Scientific Gasbench™ and Thermo Scientific ConFlo™ interfaces for isotope ratio mass spectrometry (www.thermoscientific.com).

However, a most preferred arrangement of open split is described and explained in our co-pending, as yet unpublished application nos. GB 1306806.9, GB 1306807.7 and GB 1306808.5, the contents of which are explicitly incorporated herein by reference in their entirety. In essence, the open split may be in the form of any suitable opening to atmosphere, e.g. a tube or capillary that is open to atmosphere. The open split 3 in the preferred arrangement of FIG. 2 is dimensioned so that there is a negligible pressure drop across it and so that there is no, or substantially no, gas loss due to diffusion across it. The details of how to dimension this open split are again set out in our co-pending application nos. GB 1306806.9, GB 1306807.7 and GB 1306808.5 and will not be detailed further.

A variety of different analyte gas supply arrangements may be employed, and some examples will be described in connection with FIGS. 19 to 29. Some alternative arrangements to that of FIG. 2 are also contemplated and these will likewise be described subsequently. Additional, optional components can, moreover, be included in the gas inlet system 20 in accordance with the preferred embodiments of the invention.

Linking all of the different preferred embodiments, however, is the variable volume reservoir 5. It is the variable volume reservoir 5 that permits the buffering of various analyte supplies, both continuous and pulsed, so as to permit the controlled delivery of analyte gas to the analyzer. The variable volume reservoir likewise permits auto dilution, cleaning of the gas lines, and various other advantageous procedures which will be detailed subsequently.

In general terms, the variable volume container 5 should ideally meet one or more of the following criteria:

It should be possible to adjust the container volume with a certain accuracy;

It should be possible to generate a pressure inside the volume of the reservoir 5 above or below ambient pressure, depending upon the operating steps;

The variable volume reservoir should be gas tight towards the surrounding atmosphere. The degree of gas tightness will depending upon operating conditions but may be calculated for all such operating conditions;

The variable volume reservoir should not adsorb the sample, so that the variable volume reservoir does not exhibit memory effects.

For the purposes of obtaining an accurate measurement, it is preferable to adjust the reservoir volume continuously during a measurement. This provides a constant pressure at, and/or a flow into, the analyzer. Typically a flow through the analyzer will be held constant by controlling the variable reservoir such that the pressure is constant.

Three general approaches exist. Firstly, a sensor may be connected to the reservoir to allow a feedback control of the pressure. Secondly, after calibration or calculation, the volume may be simply continuously adjusted to give a constant flow. Thirdly, feedback from the analyzer may be employed to improve the flow rate and/or pressure. Such feedback may likewise be used to update a calibrated flow control.

Various methods and devices that enable such controlled delivery as a continuous operation are shown and discussed below.

Syringe Type Variable Volume Reservoir

In the first type of variable volume reservoir 5 (FIG. 3), which is currently considered to be the preferred type, an inner cylinder (40) moves relative to a hollow outer cylinder (41) with a gas exit (42). Of course, it is not essential that the outer cylinder remains stationary whilst the inner cylinder moves and either or both of the cylinders may in fact move. It should also be appreciated that the cross section of the cylinder need not be circular and that oval or other geometric shapes are envisaged.

In the preferred embodiment of a syringe type variable volume reservoir, a shaft seal (43) is provided between the inner and outer cylinders. The volume between both cylinders represents the reservoir of variable volume. The cylinders may be formed of various materials such as glass, stainless steel, other metals, polymer materials and so forth. The shaft seal may be formed form PTFE, PFA, Viton, or other sealing materials. Should both cylinders be machined and fitted to a suitable tolerance, the shaft seal might be omitted. Alternatively, one or both of the cylinders might be partially deformable (elastic) so as to form the sealing function.

The difference of the pressure inside the variable volume reservoir 5, and atmospheric pressure, generates a force. The force may be measured, and the pressure inside the variable volume reservoir 5 can therefore be determined, within the accuracy of the friction of the sealing.

In a most preferred embodiment (FIG. 4), the outer cylinder (41) is formed of glass or stainless steel, the inner cylinder (40) is formed of a metal (typically polymer coated) and the seal (43) is formed from a PTFE or Viton material. The inner cylinder (40) is then employed as a plunger. In order to allow control of the variable volume reservoir, the plunger is connected to an actuator (44). The actuator in turn is under the control of a processor (45) so that the volume within the variable volume reservoir can be expanded or compressed at a commanded rate. In any event, a force generated between the plunger and the actuator in this case represents a measure of the pressure inside the variable volume reservoir 5. In a preferred embodiment, as noted above, the flow rate into the analyzer may be maintained at a constant rate by driving the plunger at a constant speed.

The advantage of the arrangement described here is relatively low cost and that the volume within the variable volume reservoir 5 is, at any time, strictly proportional to the distance the inner cylinder is moving relative to the outer cylinder, so that it can be controlled very accurately (since, in this case, the volume is determined by the diameter of the outer cylinder—which is fixed—and the separation between the front face of the plunger and the base of the variable volume reservoir 5).

Figure 3:
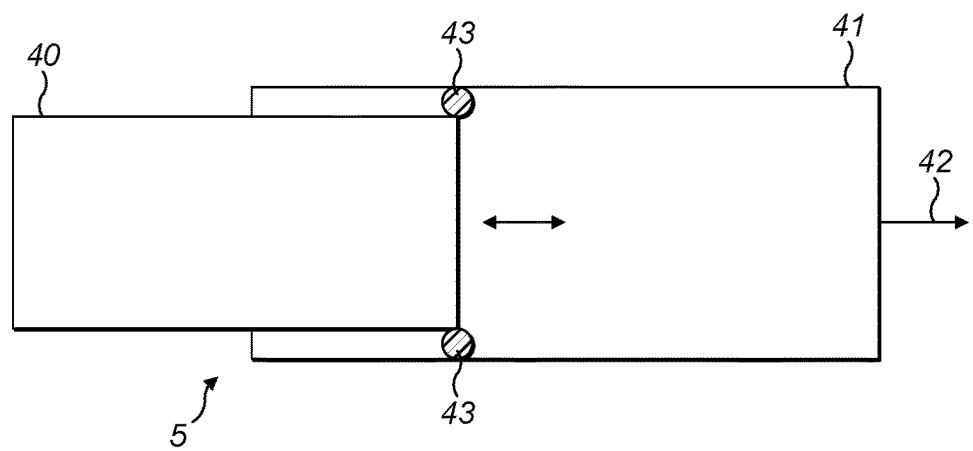
FIG. 3 shows a first embodiment of the variable volume reservoir of FIG. 2.
Figure 4:
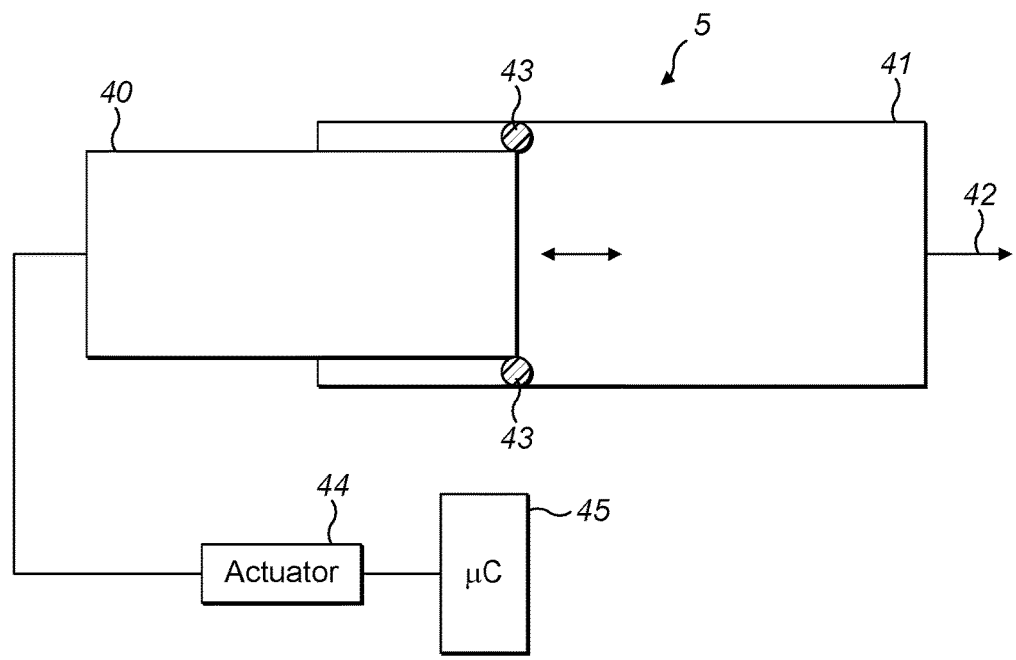
FIG. 4 shows a second embodiment of the variable volume reservoir of FIG. 2.
Figure 5:
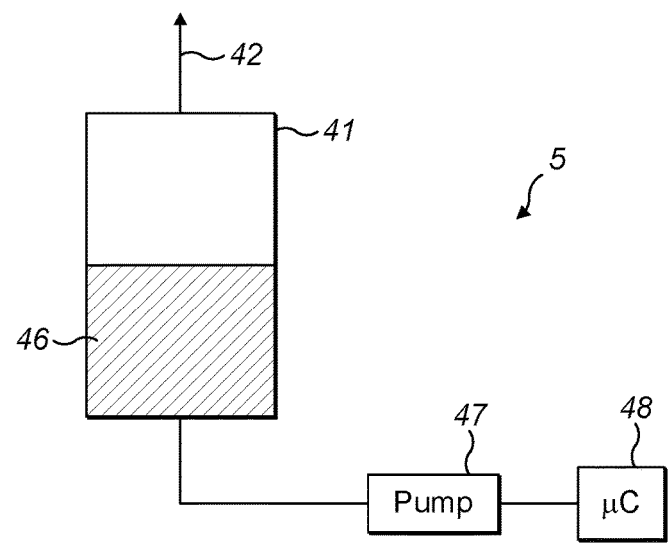
FIG. 5 shows a third embodiment of the variable volume reservoir of FIG. 2.

As still a further alternative (FIG. 5), the variable volume reservoir 5 may comprise an outer cylinder 41, the inner cylinder of FIGS. 3 and 4 being constituted by a fluid 46. The fluid can perform the sealing function and the level of the fluid (and hence the volume available to gas within the variable volume reservoir) can be controlled, e.g. by a fluid pumping device (47) connected to the cylinder, again controlled by a microcontroller (48). It will be understood that, in this case, the internal shape of the outer cylinder (41) is unconstrained since the fluid (46) forming the seal will conform to whatever shape is presented by the inner walls of the outer cylinder (41). It is, however, desirable that the exit (42) from the variable volume reservoir 5 should be located in that part of the outer volume which has a maximum distance from the centre of mass of the earth.

Figure 6:
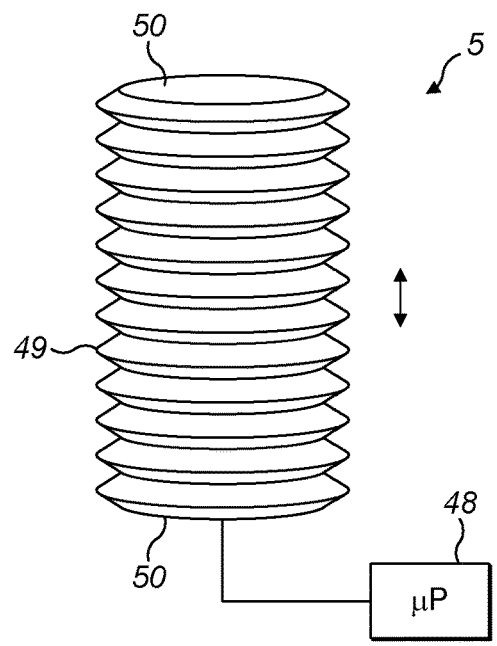
FIG. 6 shows a fourth embodiment of the variable volume reservoir of FIG. 2.

Bellows Type Variable Volume Reservoir (FIG. 6, FIG. 7) Here, the variable volume reservoir 5 is formed by upper and lower non-deformable surfaces (50) separated by compressible surrounding walls (49). Again, typically but not necessarily the variable volume reservoir is circular in cross section. The compressible surrounding walls of the reservoir 5 may be in the form of a concertina or bellows so that, to adjust the volume within the variable volume reservoir 5, each segment or sector of the surrounding walls remains adjacent to the same neighbouring sector (such that there is no sliding of multiple surrounding wall sectors relative to one another). The distance between non adjacent sections can, nevertheless, be varied (not shown), under the control of microprocessor or other controller (48).

Figure 7:
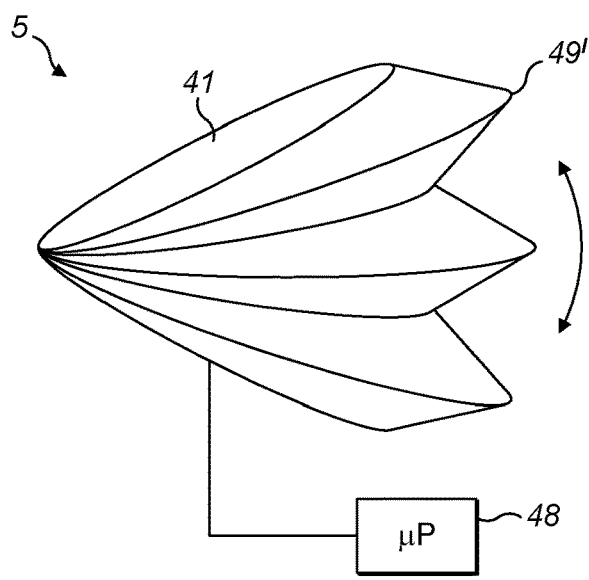
FIG. 7 shows a fifth embodiment of the variable volume reservoir of FIG. 2.

It is preferable that decrease and increase of the volume in the variable volume reservoir 5 takes place through the application of a unidirectional force, again preferably by way of a linear actuator. As shown in FIG. 7 the variable volume reservoir 5 may also employ rotational movement whereby two non-parallel planar faces 41 pivot towards and away from one another, using compressible walls 49', again under the control of an actuator (not shown) and a microprocessor (48). The retention force needed to keep the volume of the variable volume reservoir 5 constant is a measure of the pressure inside the volume. However, calibration is typically necessary because of the superposition of an elastic force resulting from deformation of the variable volume of the reservoir 5.

Again in a most preferred embodiment of a bellow type variable volume reservoir, a constant flow of gas into the analyzer may be achieved by application of a constant driving speed to the linear actuator. Moreover, welded metal may be employed to provide the bellows. Bellows cut from polymeric material might equally be employed. The advantage of the bellows type variable volume reservoir 5 is the potential extremely high leak tightness.

Bag Type Variable Volume Reservoir

Figure 8:
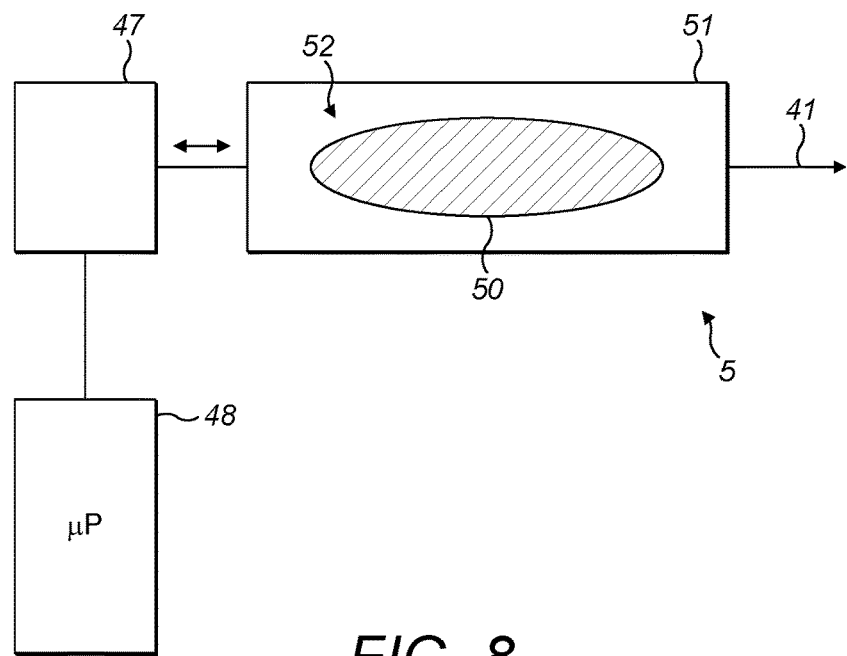
FIG. 8 shows a sixth embodiment of the variable volume reservoir of FIG. 2.

As a variation of the bellows type variable volume reservoir, and as shown in FIG. 8, a deformable bag or other deformable container (50) might be employed to provide the variable volume. Instead of collapsing or expanding surrounding walls and generally rigid upper and lower faces, the whole of the volume can be changed through the application of an isotropic force (pressure). A suitable embodiment may be a flexible container (e.g., a bag) within a rigid outer container (51). The flexible container (50) is, of course, hermetically sealed from the void (52) formed between the flexible container (50) and the rigid outer container (51) walls. The volume of the rigid outer container (51) is fixed and the volume of the inner flexible container (50) can be controlled by pumping a known amount of fluid into or out of the void (52) between the walls of the rigid outer container (51) and the flexible container (50) using a suitable pumping device (47). The pressure inside the flexible container (50), the inner of which represents the variable volume of the variable volume reservoir 5, is nearly equal to the pressure in the void (52) between the flexible container (50) and the rigid outer container (51). Thus it may be easily be determined.

Although the bag type variable volume reservoir more particularly lends itself to pressure control, nevertheless a constant gas flow rate may be achieved, for example by control using a mass flow controller (MFC).

In any of the different embodiments described above (syringe or cylinder type, bellows type or bag type variable volume reservoir 5), some general parameters and characteristics are envisaged.

The minimum volume of the variable volume reservoir should ideally be as close as possible to zero;

The maximum volume of the variable volume reservoir is optimally between about 20 and about 500 ml, and a particularly preferred range of volumes is between 100 and 200 ml;

The ratio of the maximum to minimum volume of the variable volume reservoir should preferably exceed a factor of 10;

It should be possible to change the volume of the variable volume reservoir 5 at a user definable rate;

It should be possible to specify a uniform rate of change of volume;

The maximum rate of change of volume within the variable volume reservoir 5 should be higher than the volume input rate of the isotope ratio analyzer 1;

The minimum rate of change of volume should be at least ten times slower than the maximum rate of change of volume of the variable volume reservoir 5.

The mixing of the gas within the variable volume reservoir 5 should be optimized. Optimization is achieved by considering the notional connection of two points within the variable volume reservoir 5 by a curved line. The line is constrained to be inside the container at each point, as short as possible, and continuously either rising or falling, or having no slope with respect to the gravitational centre of the earth. The length of the line for any two points within the volume of the variable volume reservoir 5 should not exceed 150 mm. The line should also be smaller than the cube root of the volume of the variable volume reservoir 5, multiplied by a factor of 5 (or 10). The volume v within the variable volume reservoir 5 is defined by $(V_{min}+(V_{max}-V_{min}))*0.1<V<V_{max}$ With $V_{min}$=minimum Volume, $V_{max}$=maximum volume In this configuration, the gas supply lines/capillaries and so forth are not taken into account.

Likewise, in common with each of the various embodiments of variable volume reservoirs 5, the exit of the reservoir 5 should preferably be at approximately half the height or at least not in the top or bottom 20% of the height. This arrangement minimises mixing effects caused by diffusion of the gases as diffusion is at a minimum rate in this middle section.

Another consideration to minimize mixing effects is the position of the gas exit from the variable volume reservoir 5. If different gases are filled into the volume subsequently, the different gases typically have a different specific weight. Thus, they will be "stacked" horizontally. In the following, the gases will mix by diffusion effects.

The degree of mixing of course increases with time. But it is also observed that mixing effects are less pronounced in the "middle" section, that is, neither at the top nor at the bottom of the variable volume reservoir 5 (here, the terms "top" and "bottom" are meant in the gravitational sense). Therefore, a preferred embodiment of the invention locates the gas entry/exit towards the "middle" of the height—and, at least, not in the top or bottom 20% of the height of the variable volume reservoir.

Also, it is preferred if the variable volume is "flat". In the case of a syringe this means that it is preferred if the syringe is positioned horizontally rather than vertically.

Optimising the mixing of gas inside the variable volume reservoir 5 as detailed above, and locating the exit of the container neither at the top nor at the bottom of the variable volume reservoir 5 ensures that mixing inside the volume by diffusion is facilitated.

The currently most preferred arrangement for a variable volume reservoir is a glass syringe having a maximum volume of around or in excess of 100 ml, controlled by a stepper motor.

Having described a number of preferred embodiments for the variable volume reservoir 5, various different configurations of the gas inlet system embodying the present invention will now be described, referring once again, initially, to FIG. 2.

I First Configuration: Use of Carrier Gas to Supply Analyte to Analyzer

In the first implementation of the gas inlet system of FIG. 2, the second supply valve 6 is closed at all times so that the second source of analyte gas 11 is always isolated. At the start of any measurements, the variable volume reservoir 5 is compressed so as to contain a minimum volume (typically, zero or substantially zero).

(i) Analyte Collection

Analyte gas is supplied from the first source of analyte gas 9. The analyte gas supply from the first source of analyte gas 9 is entrained with carrier gas. The flow of carrier gas and entrained analyte is continuous in the embodiment of this section of the description.

Prior to filling the variable volume reservoir 5, the first source of analyte gas 9 is connected via the first supply valve 7 to the second open split 8. In this case, analyzer valve 4 is closed, and so is second supply valve 6, so that, with the variable valve reservoir 5 in an initial minimal volume configuration, there is no gas flow through the connecting gas lines between the analyzer valve 4, the first supply valve 7, the second supply valve 6 and the inlet/outlet from the variable volume reservoir 5.

Analyte collection may be achieved, in the gas inlet system embodying the present invention, in two different modes of operation, either by sampling the whole analyte for a certain time period, or by splitting away part of the analyte entrained in the continuous carrier gas supply from the first source of analyte gas 9 with a part flowing directly into the analyzer 1.

(a) Sampling the Whole Analyte

In the following description, a series of steps are described. The skilled reader will readily appreciate that, unless the context so requires, the order of the steps is not critical to the resultant configuration and effect. The skilled person will also recognise that, whatever the order of the steps, a delay, or no delay, may be present between one, some or all of the steps.

Referring again to FIG. 2, to commence sampling of the whole analyte, the analyzer valve 4 is first opened. The first source of analyte gas 9 is next connected to the variable volume reservoir 5 by manipulation of first supply valve 7.

Figure 9:
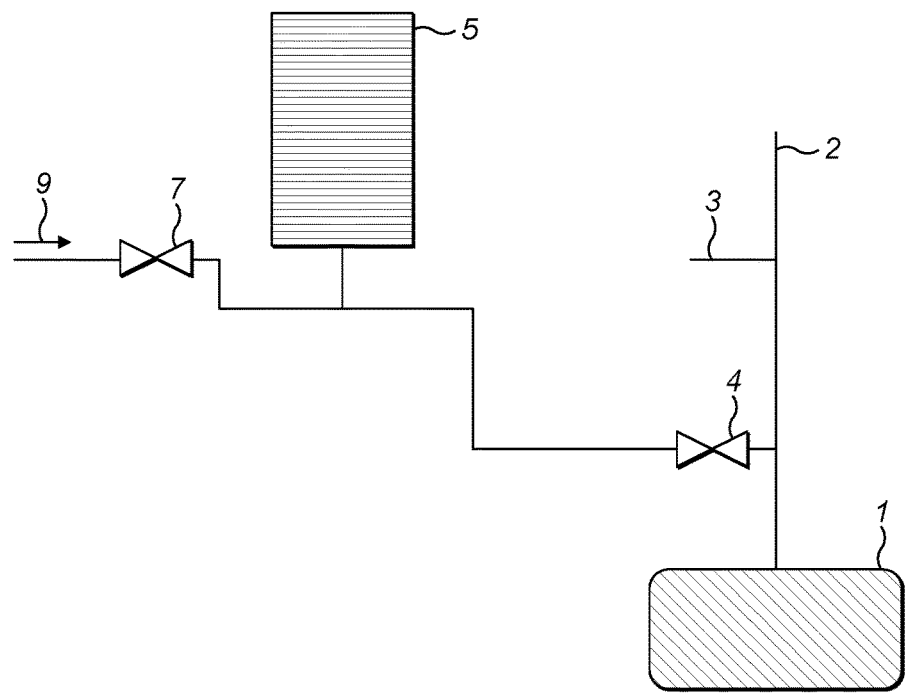
FIG. 9 shows the gas inlet supply of FIG. 2 in a first configuration.

The resultant configuration of the gas inlet system of FIG. 2 is shown schematically in FIG. 9. Those parts of the system 20 which are isolated and not relevant to the following explanation of sampling of the whole analyte have been excluded for clarity in FIG. 9.

The carrier gas supply 2 supplies a carrier gas flow which is larger than the intake of the analyzer 1 by an amount x. This means that, in the case where the analyzer valve 4 is closed, the entire amount of x, representing the difference between the analyzer gas intake and the carrier gas supply, will flow through the first open split 3 to atmosphere or to another device having a constant pressure. In the arrangement of FIG. 9, however, the analyzer valve 4 is open. The variable volume reservoir 5 is expanded at a rate which is higher than the gas flow from the first source of analyte gas 9. Moreover, the difference between the rate of expansion of the variable volume reservoir and the gas flow from the first source of analyte gas 9 is smaller than the amount x which, as explained above, represents the difference between the maximum analyzer gas intake and the carrier gas supply. The extent to which the difference between the rate of expansion of the variable volume reservoir and the gas flow from the first source of analyte gas 9, is smaller than this amount x, is determined by the type of the carrier gas and dimensions of the first open split 3. It is, in fact, possible for each combination of carrier gas type, open split dimensions, and tolerable loss through diffusion, to determine a value for how much small the above difference must be. The carrier gas supplied from source 2 may be, for example, dry air, or zero air, or helium, or nitrogen, or argon, or generally a gas or similar, but not identical, composition to the analyte gas.

In consequence of this particular configuration, variable volume reservoir 5 advantageously is filled with the whole of the flow from the first source of analyte gas 9, plus also an amount of flow from the carrier gas supply 2, via the first open split 3. In this way, the whole sample is transferred into the variable volume container, along with carrier gas from the carrier gas supply 2.

(b) Splitting Away Part of the Analyte

As in the sampling of the whole analyte in (a) above, again with the gas inlet system in the initial configuration (variable volume reservoir at the minimum volume, valves 4, 6 and 7 closed), the analyzer valve 4 is opened. The first source of analyte gas 9 is connected to the variable volume reservoir 5. As previously, valve 6 is closed. Thus in this configuration, the gas inlet system is functionally as illustrated in FIG. 9 once more.

The variable volume reservoir 5 is then expanded at a rate which is this time lower than the gas flow from the first source of analyte gas 9. Any flow of gas from the first source of analyte gas 9 in excess of the uptake capacity of the variable volume reservoir 5 (on account of its relatively slow rate of expansion) then flows through the valve 4 and is sucked into the analyzer 1 along with carrier gas from the carrier gas supply 2.

If the difference between the flow into the variable volume reservoir 5 and the sample flow from the first source of analyte gas 9 is larger than the uptake of the analyzer 1, then any excess analyte gas is passed along the carrier gas supply line to the first open split 3. Although this particular implementation is not preferred, nonetheless it can be advantageous when the sample amount is known to be very high, since, in that case, even if the flow from the first source of analyte gas 9 is not known, the gas composition flowing into the analyzer 1 will be certain to be identical to the gas composition both from the first source of analyte gas 9 and at the variable volume reservoir 5.

More generally, the advantages of splitting away part of the analyte are:
  There is no dilution of the sample between the first source of analyte gas 9 and the variable volume reservoir 5.
  During the sampling process, the concentration of the analyte gas can be monitored using the analyzer 1. Even though only a small fraction of the sample deriving from the first source of analyte gas 9 actually flows into the analyzer 1, it may be sufficient to permit rough determination of the sample amount. This in turn can be used to ascertain the sample concentration in the variable volume reservoir 5. It can also be used to address the challenges presented by analyte gas in the form of a peak or pulse. In this case, the concentration of analyte within the gas flowing from the first source of analyte gas, relative to the continuous supply of carrier gas in which it might be entrained, is at or substantially at zero. It then increases for a certain time and then decreases again until it reaches or approaches zero. To address this, either the whole peak may be transferred into the variable volume reservoir 5, or a constant split ratio of this peak may be transferred into the variable volume reservoir 5 instead. Alternatively, sampling may be terminated at the end of the peak or pulse.

For both applications, measuring the sample concentration during the sampling process can be useful. To permit this, however, it is desirable that both the volume of the variable volume reservoir 5, and the time derivative of that, and the flow of analyte gas from the first source of analyte gas 9 can be controlled sufficiently accurately. For this reason, the syringe type variable volume reservoir 5, as described above, provides particular advantages.

Moreover, it is desirable either to control the flow from the first source of analyte gas, for example by using a mass flow controller (mfc), a proportional valve, a volume flow controller or a similar device, or by measuring the flow from the first source of analyte gas 9 using a mass flow meter or the like.

Figure 10:
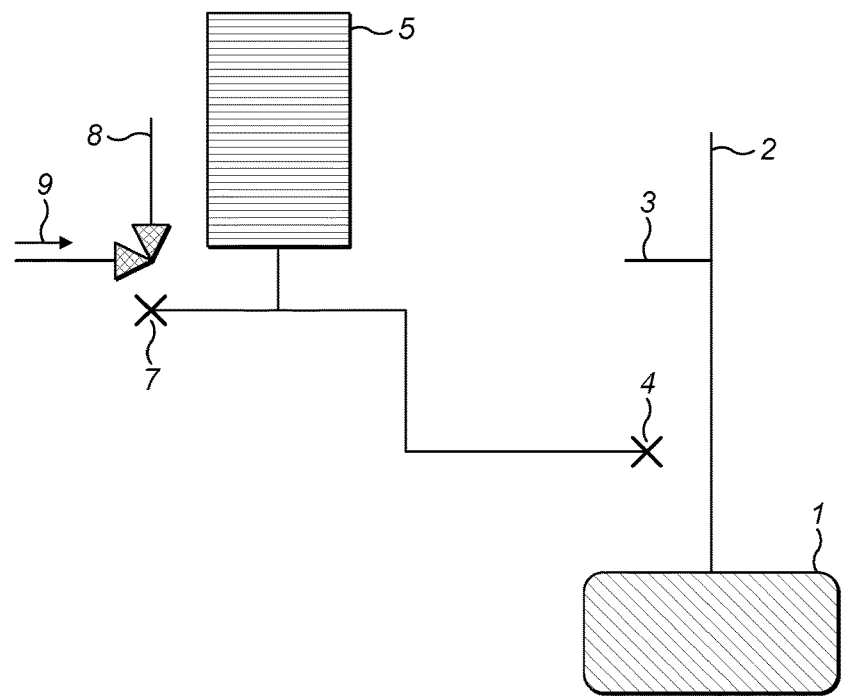
FIG. 10 shows the gas inlet supply of FIG. 2 in a second configuration.

Collection of analyte within the variable volume reservoir 5 can be terminated at any point between the minimum and maximum volumes of the variable volume reservoir. To do this, the following steps are taken. Firstly, the variable volume expansion of the reservoir 5 is stopped. Next, the first supply valve 7 is switched so that the first source of analyte gas 9 is once again connected to the second open split 8. The analyzer valve 4 is also then closed. The resultant configuration is shown in FIG. 10. Assuming that there are no leaks within the variable volume reservoir 5, the valves 4 and 7, and the supply lines that connect these, the volume pressure within the variable volume reservoir 5 then remains constant until it is desired to, for example, measure the analyte that has been stored.

(ii) Preparation for Measurement

Various optional steps may be taken in preparation for measurement of the analyte.

(a) Determination of Aanalyte Concentration

If the variation in the amount of sample is small and falls within the linearity range of the analyzer 1, then no further action is necessary and measurement may commence directly.

If the user knows the amount of analyte at least some extent, then the concentration within the variable volume reservoir 5 can be calculated from the known values of the relevant flows and volumes.

If the procedure for splitting away part of the analyte (I(i)(b) above) has been employed, then, knowing the concentration of the split away gas, and the flow rates, concentration within the variable volume reservoir can be calculated.

Otherwise, part of the gas that has been stored in the variable volume container (I(i) above) can be used to determine the concentration of analyte within the volume of the variable volume reservoir. To do this, starting with the valves in the configuration shown in FIG. 10 wherein the analyzer valve 4 and the second supply valve 6 (FIG. 2) are closed, and the first supply valve 7 is set to connect analyte source 9 to open split 8, the volume of the variable volume reservoir 5 is decreased to a known amount. Next, the analyzer valve 4 is opened and the concentration of the analyte is determined and integrated using the analyzer 1.

It is feasible to carry out the determination of concentration of the analyte within the variable volume reservoir without first closing the analyzer valve 4 This is the preferred mode of operation as no pressure peak is generated downstream of the analyser valve 4 after opening it. This way, it is ensured that no gas is lost through the open split 3. As a final alternative for determination of the concentration of analyte, it may be carried out during measurement of the analyte itself, rather than as a preliminary step.

(b) Auto Dilution: Split Away Part of the Sample

It may be that the concentration of analyte within the variable volume reservoir 5 once it has been collected is too high for the subsequent measurement. In this case, it is desirable to dilute the sample within the variable volume reservoir 5.

Figure 11:
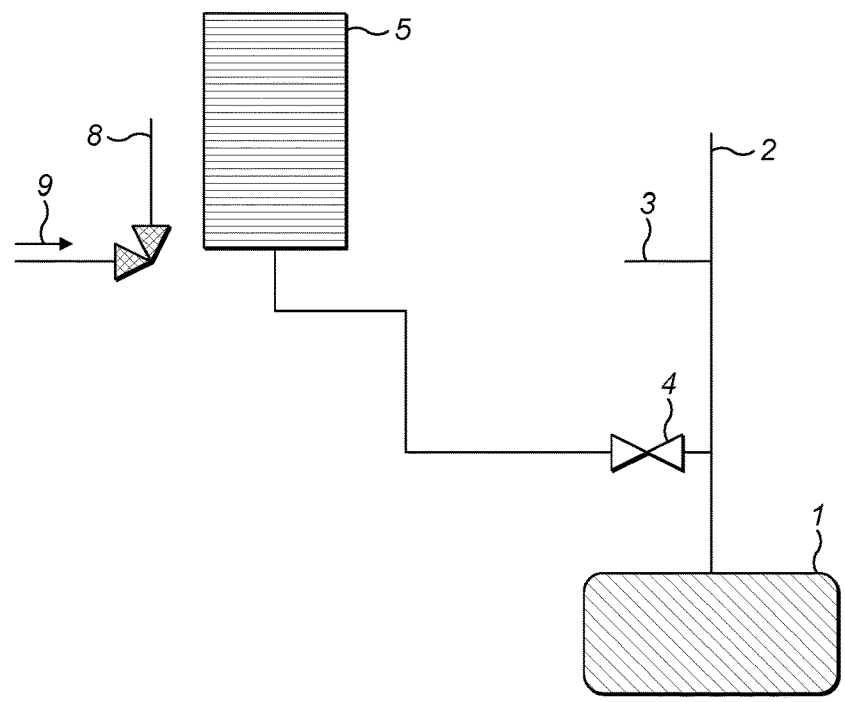
FIG. 11 shows the gas inlet supply of FIG. 2 in a third configuration.

To achieve this, the first supply valve 7 is configured to connect the first source of analyte gas 9 to the second open split 8. The second supply valve 6 is closed so as to isolate the second source of analyte gas 11. The analyzer valve 4 is open. Thus the configuration of the gas inlet system 20 is as shown in FIG. 11. The volume of the variable volume reservoir 5 is decreased by a known amount. Some of the gas within the variable volume reservoir 5 flows through the analyzer valve 4 to the analyzer 1. The remainder (that is, the flow of gas in excess of the capacity of the analyzer) flows to the first open split 3.

Next, the volume of the variable volume reservoir 5 is increased again to a desired amount. The speed of volume increase should be smaller than the difference between the uptake of the analyzer 1, and the carrier gas flow from the carrier gas supply 2. In that case, the variable volume reservoir 5 sucks in carrier gas from the carrier gas supply 2. Mixing takes place so that the resultant concentration of analyte within the variable volume reservoir 5 is lower at the end of the procedure than at the beginning.

(c) Pre-adjust the Pressure Inside the Variable Volume Reservoir

In the idealized situation that there is no flow restriction between the variable volume reservoir 5 and the analyzer valve 4, the flow of gas at the analyzer valve 4 would always be equal to the time derivative of the volume of the variable volume reservoir 5. It is thus desirable that the restriction between the variable valve reservoir 5 and the analyzer valve 4 is as small as possible. Where the restriction is considered non-negligible, it is necessary to take into account the fact that the gas flow through the analyzer valve 4 depends upon the pressure inside the variable volume reservoir 5 and also upon the restriction. The pressure must first be built up. In mathematical terms:

$$\frac{\partial}{\partial t}p(t) = -\frac{I_{-out}}{V(l)} + \frac{\frac{\partial}{\partial t}V(t)}{V(l)} = -\frac{p(t)}{R\,V(l)} + \frac{j\_res}{V(l)} \quad \text{Equation 1}$$

Where p is the pressure within the variable volume reservoir 5, V is the volume within the variable volume reservoir 5, R is the restriction, $j_{out}$ represents the flow rate of gas through the analyzer valve 4; $j_{res}$ is the rate of change of volume, dV(t)/dt of the variable volume reservoir 5.

There is a steady state, in which $p=j_{res}*R$. This steady state is characterized by a steady flow of gas through the analyzer valve 4 ($j_{out}$). In order to reach this steady state as fast as possible, analyzer valve 4 and second supply valve 6 are closed, and first supply valve 7 is arranged so as to connect the first source of analyte gas 9 to the second open split 8. This is the configuration shown in FIG. 10.

Next, the volume V within the variable volume reservoir 5 is decreased until p is reached. This can be calculated from the (known) volume of the variable volume container, and the known start pressure, which will be atmospheric pressure, because the variable volume reservoir has been connected to the first open split 3.

Finally, the analyzer valve 4 is opened so as to provide the configuration shown in FIG. 11.

(d) Determining the Optimum Equilibrium Flow into the Analyzer

Prior to measurement, the optimum equilibrium flow into the analyzer is determined according to the following equation:

$$j_{res} = j_{analyzer} * (c_{analyzer}/c_{res}) \quad \text{Equation 2}$$

Where $j_{res}$ represents dV(t)/dt of the variable volume container reservoir; $j_{analyzer}$ represents the flow of gas into the analyzer; $c_{analyzer}$ represents the desired concentration of analyte within the analyzer 1, and $c_{res}$ represents the determined or estimated concentration of analyte in the variable volume reservoir 5.

In this manner, using the variable volume reservoir, the dynamic range of the setup is significantly increased, because the speed of the volume change may be adjusted across a wide range. It has been measured and shown that, in this manner, a factor of at least 25 in the dynamic range can be achieved. This has to be multiplied by the dynamic range of the analyzer 1.

(iii) Measurement

Measurement of the analyte in the variable volume reservoir is commenced (again, the order or steps is arbitrary) with the gas inlet system 20 configured as shown in FIG. 10, with the second supply valve 6 closed, the analyzer valve 4 closed, and the first supply valve 7 directing the first source of analyte gas 9 to the second open split 8. The volume of the variable volume reservoir 5 commences a decrease and at this point the analyzer valve 4 is opened so as to result in the configuration shown in FIG. 11. Data is then acquired from the analyzer 1 in known manner.

Figure 12:
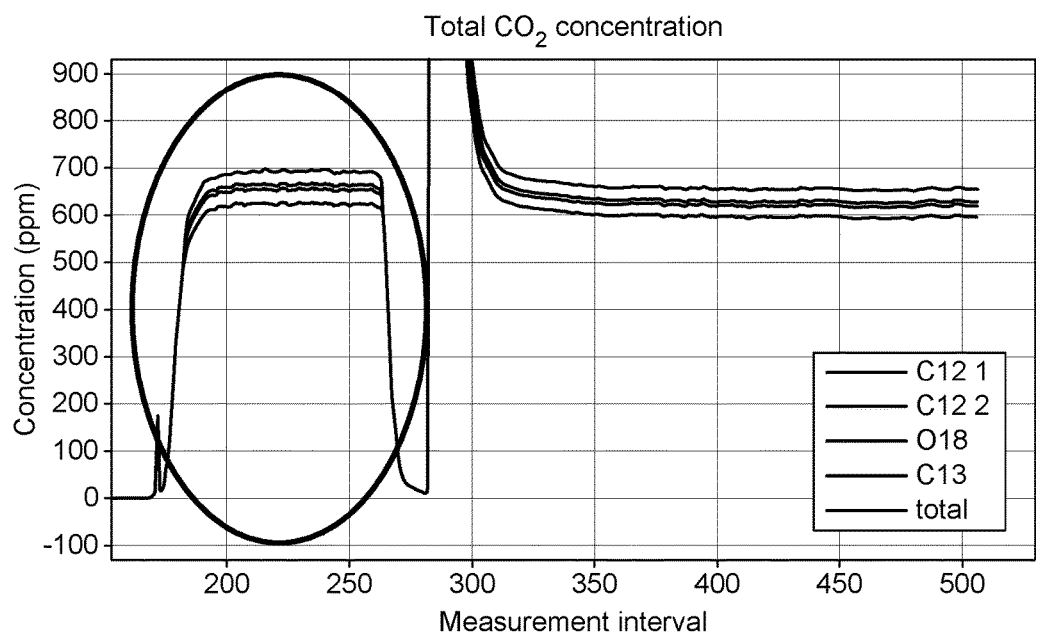
FIG. 12 shows a first plot of analyte concentration in the spectrometer vs. time when employing a gas inlet supply in accordance with embodiments of the present invention.

As has been explained above, it is advantageous to have a steady, constant flow of analyte gas into the analyzer 1. Thus, the decrease of the volume of the variable volume reservoir should preferably be constant with time. Tests have shown that it is possible to generate a constant analyte flow into the analyzer 1 using the configuration of FIG. 2/FIG. 11. A plot of the analyte concentration (vertical axis) within the analyzer as a function of time (horizontal axis) (in seconds) is shown in FIG. 12. Measurement ceases after the variable volume reservoir 5 reaches its minimum volume or, alternatively, if it is determined that sufficient time has elapsed for the acquired accuracy to have been reached. Where the measurement ceases before the volume of the variable volume reservoir 5 has reached its minimum, it is desirable then to fast set the variable volume reservoir to its minimum volume. This can be done simply by increasing the rate of compression of the variable volume reservoir with the analyzer valve 4 still open. Any gas flow in excess of the ability of the analyzer 1 to accept it is removed via the first open split 3.

Figure 13:
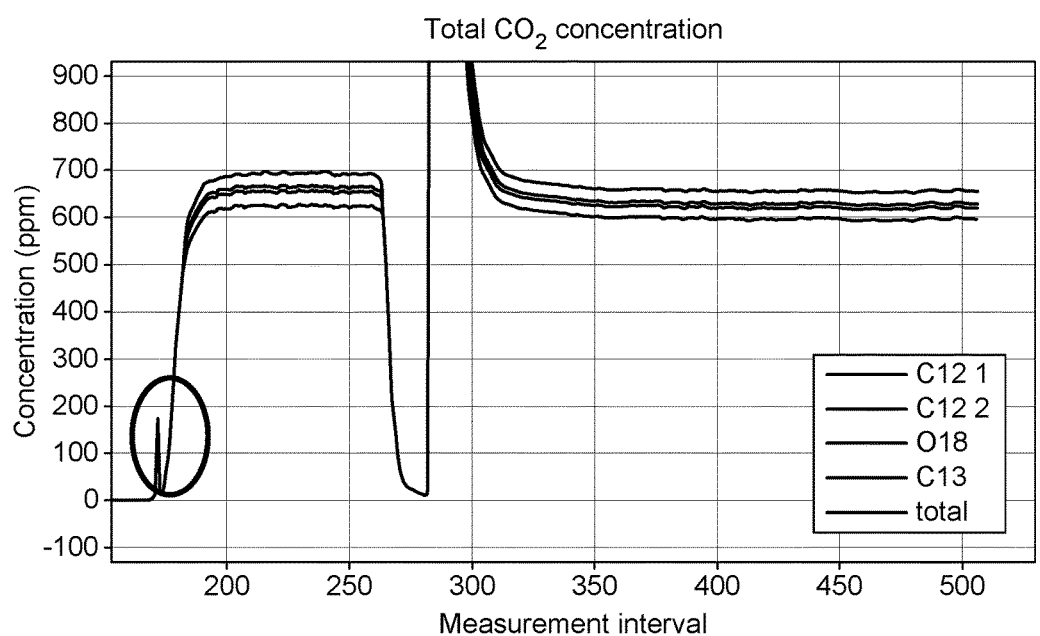
FIG. 13 shows a second plot of analyte concentration in the spectrometer vs. time when employing a gas inlet supply in accordance with embodiments of the present invention.

At the commencement of measurement of the analyte, it is possible to adjust the analyte flow into the analyzer 1. A plot of analyte concentration in the analyzer 1 as a function of arbitrary time (horizontal axis) is shown in FIG. 13; the initial peak to the left of the plot has been circled. The rise in intensity at the beginning of the measurement is determined, amongst other factors, by the concentration of the analyte: thus, it can be used to determine and adjust the optimum final flow into the analyzer within a very short period of time.

(iv) Cleaning of the Gas Lines and the Variable Volume Reservoir

Typically, the minimum volume of the variable volume reservoir 5 is as close as possible to zero. Likewise, the volume of the various gas transport lines within the gas inlet system is preferably as close to zero as possible. On that basis, memory of remaining gas inside the lines and the variable volume reservoir can often be neglected.

If not, however, then following measurement (in particular, prior to filling the variable volume reservoir with fresh analyte for subsequent measurements), the gas supply lines and the variable volume reservoir 5 can be flushed with zero air (i.e., air free of $CO_2$) using the following procedure.

Firstly, the second supply valve 6 is closed and the first supply valve 7 is configured to connect the first source of analyte gas 9 to the second open split 8. Analyzer valve 4 is open. The configuration of the gas inlet system is thus as shown in FIG. 11.

The volume of the variable volume reservoir 5 is decreased to a minimum volume. Any gas remaining within the variable volume reservoir 5 thus leaves the system through the analyzer valve 4 and the first open split 3.

Next, the volume of the variable volume reservoir 5 is increased again. The speed of the volume increase of the reservoir 5 should be smaller than the difference between the analyzer uptake capacity and the carrier gas flow from the carrier gas supply 2. In this case, the variable volume reservoir 5 is then filled up with carrier gas from the carrier gas supply 2.

Once the variable volume reservoir has been filled with carrier gas, that carrier gas can be expelled again by cyclically repeating the above steps one or more times (i.e. flushing the carrier gas in the variable volume reservoir back out through the supply lines to the first open split 3).

(II) Sampling of a Limited Sampling Amount by Vacuum

For this type of sampling the first supply valve 7 is effectively closed relative to the variable volume reservoir 5 i.e. the first source of analyte gas 9 is connected to the open split 8 and therefore not to the variable volume reservoir 5.

In the alternative implementation of embodiments of the present invention, a second source of analyte gas 11 is supplied to the analyzer using the variable volume reservoir 5. In each of the following sections, the second source of analyte gas 11 is connected into the gas inlet system through a port 10. It is preferable that connection and disconnection between the second source of analyte gas 11 and the gas inlet system 20 is straightforward. The removable coupling described has a screw thread and is preferably a finger tight connector, as used in liquid chromatography, with a preferred thread style of either 10-32 coned, or ¼-28 coned, or 10-32 flat bottom or ¼-28 flat bottom. A Cajon port may be employed instead.

(i) Analyte Collection

Referring once again to FIG. 2, this time, to collect analyte from the second source of analyte gas 11, the variable volume reservoir 5 is set to minimum volume. The analyzer valve 4 is closed and the second supply valve 6 is opened so as to connect the second source of analyte gas 11, via the removable coupling, to the variable volume reservoir 5. The first source of analyte gas 9 is connected to the second open split 8 by appropriate configuration of the first supply valve 7.

Figure 14:
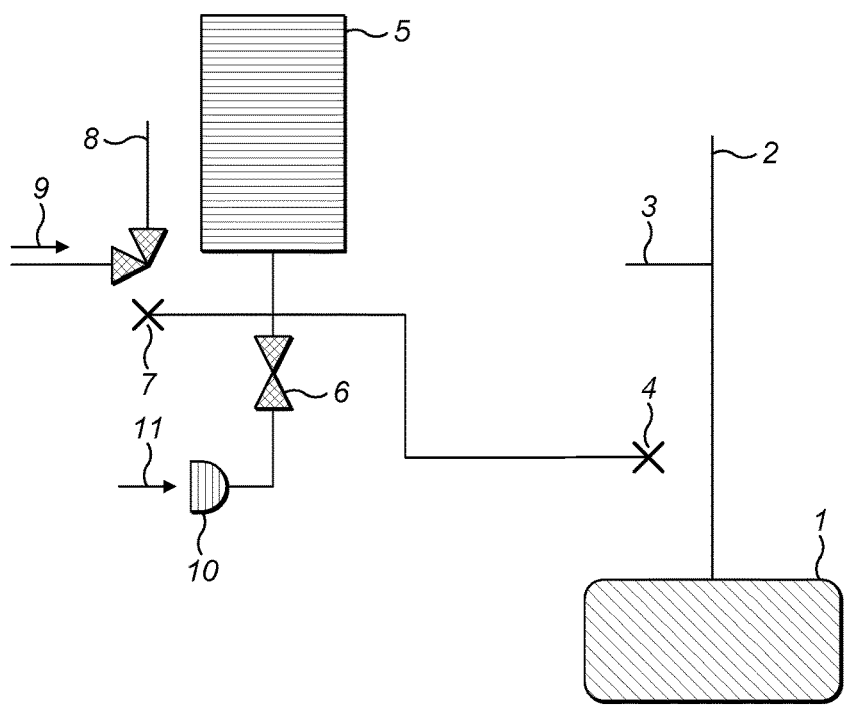
FIG. 14 shows the gas inlet supply of FIG. 2 in a fourth configuration.

Functionally, the configuration is as shown in FIG. 14.

The volume of the variable volume reservoir 5 is then increased. The second supply valve 6 is then closed again so that, functionally, the arrangement of FIG. 2 is as shown in FIG. 10, with the variable volume reservoir 5 isolated both from the analyzer/carrier gas supply and first open split 3, and also from the first and second sources of analyte gas 9,11.

Depending upon the type of sampling container that represents the second source of analyte gas 11 (some examples of which will be described in further detail below), there will now be a (partial) vacuum inside the variable volume reservoir 5. Thus, the volume of the variable volume reservoir 5 is decreased again until the pressure inside it reaches atmospheric pressure. The amount of decrease necessary can either be calculated from the known volume of the reservoir 5 according to the following expression:

$$\frac{\Delta V}{V} = \frac{V_{sc,min}}{V + V_{sc,min}} \quad \text{Equation 3}$$

Where $V_{sc,min}$ is the minimum volume of the sampling container (i.e. variable volume reservoir 5)—which may be zero—and V is the volume of the variable volume reservoir 5 following introduction of analyte. Alternatively, the pressure in the variable volume reservoir 5 can be measured and set to atmospheric pressure. Techniques for pressure measurement are set out above as part of the description of some preferred embodiments of variable volume reservoir 5.

(ii) Preparation for Measurement (a) Determination of Analyte Concentration

As with the continuous carrier gas supply embodiments described above in Section I(ii), various optional steps may be taken in the preparation for measurement. Determination of analyte concentration is essentially as described in Section I(ii)(a) above. Either the variations of the amount of sample are small and fall within the linearity range of the analyzer 1, so that no actions are necessary, or the user may know the amount to some extent so that the concentration within the variable volume reservoir 5 can be calculated from the known flows and volumes, or part of the gas within the variable volume reservoir 5 may be used to determine the concentration of analyte within that reservoir 5. The technique is as described above in I(ii)(a): the analyzer valve 4 and the second supply valve 6 are closed and the first supply valve 7 is set to connect the first source of analyte gas 9 to the second open split 8. The volume within the variable volume reservoir 5 is then decreased to a known amount. The analyzer valve 4 is then opened and the concentration of the analyte is determined and integrated using the analyzer 1. Again, by analogy, it is possible to carry out this procedure with the analyzer valve 4 left open but that is not the preferred technique.

(b) Auto-dilution: Splitting Away of Part of the Sample

The procedure for diluting the concentration of analyte within the variable volume reservoir 5 by splitting away part of the sample is identical to that described in Section I(ii)(b) above.

(c) Pre-adjustment of the Pressure Inside the Variable Volume Reservoir

Likewise, the procedure here is exactly the same as in Section I(ii)(c) above.

(iii) Measurement

Measurement of the analyte within the analyzer 1 employs the same technique as described in I(iii) above.

(iv) Cleaning of the Gas Lines and the Volume

Figure 15:
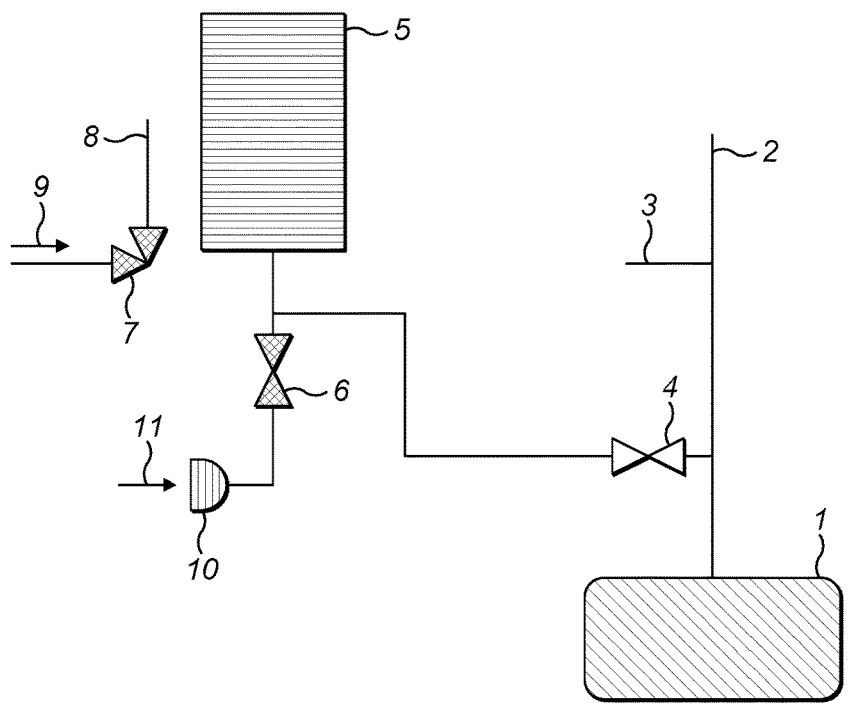
FIG. 15 shows the gas inlet supply of FIG. 2 in a fifth configuration.

Again, similar considerations apply as with the use of a continuous analyte gas supply as described in Section I(iv) above. The variable volume reservoir 5 and gas supply lines can be flushed with zero air prior to commencement of analysis. The second supply valve 6 is closed and the first supply valve 7 is configured to connect the first source of analyte gas 9 with the second open split 8. The analyzer valve 4 is opened. The configuration of the gas inlet system configuration is thus as shown in FIG. 15. Next, the volume of the variable volume reservoir 5 is decreased to the minimum volume so that the gas, if any, within the variable volume reservoir 5 leaves the gas inlet system through the first open split 3.

Next, the analyser valve 4 is closed and the second supply valve 6 is opened, so that the volume of the variable volume reservoir 5 is increased. This creates a vacuum between the first supply valve 7, second source of analyte gas 11, variable volume reservoir 5 and the analyser valve 4. The gas between the second supply valve 6 and the second source of analyte gas 11 is now distributed over the whole volume between the first supply valve 7, second source of analyte gas 11, variable volume reservoir 5 and the analyser valve 4. Hence the amount of gas between the second supply valve 6 and the second source of analyte gas 11 is significantly decreased. Next, the second supply valve 6 is closed so that the volume of the variable volume reservoir 5 is decreased to the minimum volume. The analyser valve 4 is opened again so that any gas between the first supply valve 7, second source of analyte gas 11, variable volume reservoir 5 and the analyser valve 4 is released through the open split 3.

The volume of the variable volume reservoir 5 is then increased again at a rate sufficiently slow enough to ensure that only carrier gas, rather than air, enters the volume between the first supply valve 7, second source of analyte gas 11, variable volume reservoir 5 and the analyser valve 4 via the open split 3. The rate at which the volume increases should be less than the difference between the rate of uptake by the analyser 1 and the rate of carrier gas flow from the carrier gas supply 2. At this stage the region between the first supply valve 7, second supply valve 6, variable volume reservoir 5 and the analyser valve 4 is filled with carrier gas and there is a vacuum between the second supply valve 6 and second source of analyte gas 11. To fill this region with carrier gas, the analyser valve 4 is closed and the volume of the variable volume reservoir 5 is decreased to generate an overpressure. This overpressure needs to be large enough so that once the second supply valve 6 is opened the pressure is still higher than atmospheric pressure. This procedure may be repeated several times.

III Optional Further Features of the Gas Inlet System

Figure 16:
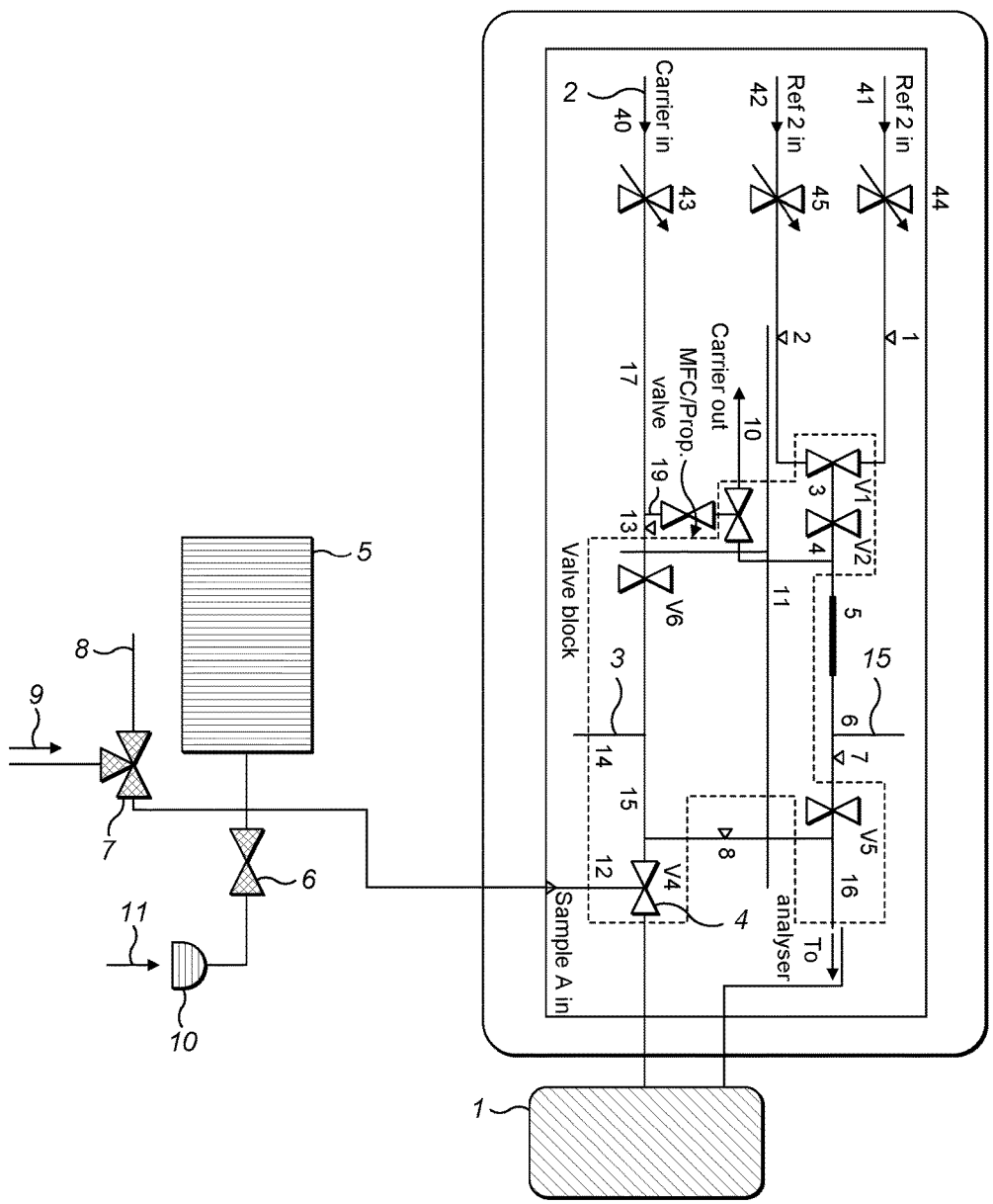
FIG. 16 shows the gas inlet supply of FIG. 2, but further including a reference gas supply.

FIG. 16 shows the further introduction of the particular form of gas inlet system described in our co-pending application nos. GB 1306806.9, GB 1306807.7 and GB 1306808.5. The arrangement described in that co-pending application is suitable for the provision of carrier gas from source 2, the first open split 3 and the analyzer valve 4. However, within the arrangement, it is also possible to provide a referencing unit identified generally at reference numeral 15 in FIG. 16. The referencing unit, as is described in our co-pending application nos. GB 1306806.9, GB 1306807.7 and GB 1306808.5, permits linearity calibration and delta scale contraction by providing mixtures of reference gas (e.g. $CO_2$) with carrier gas, and using reference gas from two different sources with different known isotope ratios. The arrangement shown in FIG. 16 provides a convenient way to supply these different concentration gases to the analyzer 1, for example, by mixing pure $CO_2$ with $CO_2$ free air (known as zero air) or other $CO_2$ free gas. For further details of the referencing unit 15 the skilled reader is directed to our co-pending application nos. GB 1306806.9, GB 1306807.7 and GB 1306808.5. The analyte and reference gas flows are preferably adjusted so that they show a similar intensity when measured in the spectrometer, e.g. by adjusting the analyte gas flow as described herein to match the reference gas flow.

Figure 17:
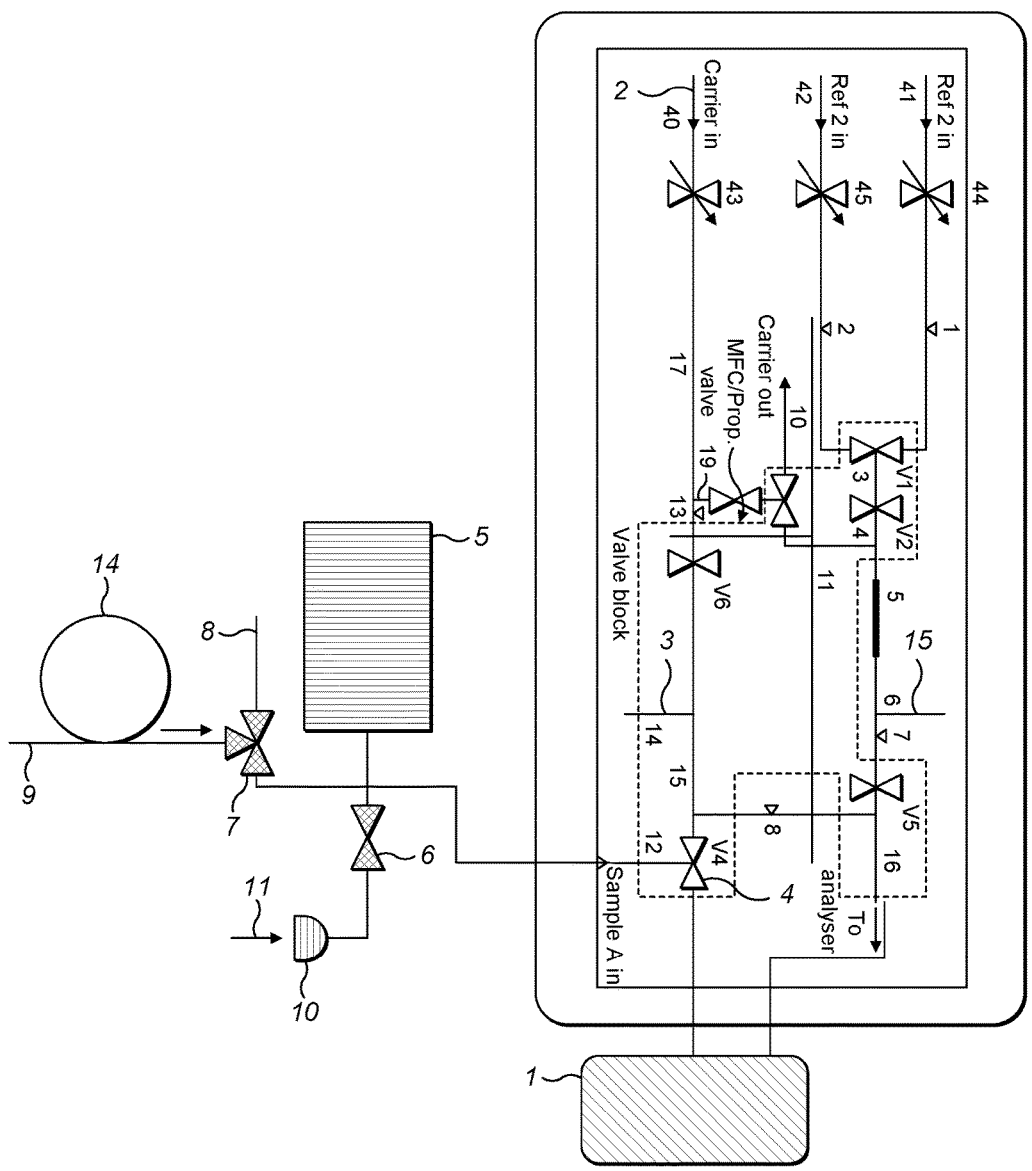
FIG. 17 shows the gas inlet supply of FIG. 11, and further including a water dryer.

FIG. 17 shows the arrangement of FIG. 16 with still a further additional component, namely a water drier (a Nafion trap) 14. The water drier is located in line between the first source of analyte gas 9 and the first supply valve 7 so as to dry the analyte gas.

Further additional or alternative components may be employed. For example, chemical and/or cryo traps may be employed along the first and/or second analyte gas supply lines from the first and second sources of analyte gas 9,11, in order to remove unwanted gases from the analyte stream.

Figure 18:
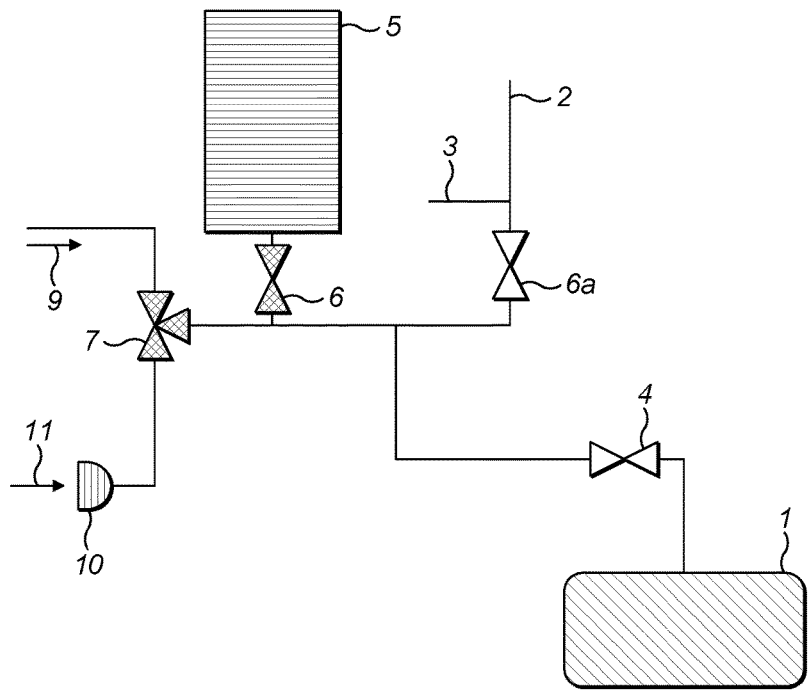
FIG. 18 shows a second embodiment of a gas inlet supply for a spectrometer exemplifying the present invention.

Although the arrangement of FIG. 2 represents a preferred arrangement of a gas inlet system embodying the present invention, other, similar set ups having the same functionality are envisaged. One example is shown in FIG. 18. In FIG. 18, the first and second sources of analyte gas 9,11 are each connected to separate removable couplings of a three way supply valve 7. The third removable coupling of the supply valve 7 is connected via a second supply valve 6 to a variable volume reservoir 5. The variable volume reservoir 5 is selectively connectable to an analyzer 1 via an analyzer valve 4. The gas supply line connecting the second supply valve 6 in communication with the variable volume reservoir 5 with the analyzer valve 4 and analyzer 1 branches at a location between the second supply valve 6 and the analyzer valve 4; a carrier gas supply line is connected to that branch point via a third supply valve 6a. Between the carrier gas supply 2 that supplies gas via the third supply valve 6a and that third supply valve 6a is a first open split 3.

In general terms, in addition to the variable volume reservoir 5 embodiments of the present invention may include one or more of the following components: at least one open split, a plurality of valves to allow isolation of the variable volume reservoir 5 from the open split or splits, at least one inlet port and, if there are several inlet ports, suitable valves to switch between them, a connection to the analyzer, and a connection to the carrier gas supply.

Analyte Gas Supply

Various methods for the delivery of analyte gas to the gas inlet system embodying the present invention are envisaged. This may be separated, generally, into specific arrangements for the delivery of a continuous flow of analyte gas (that is, suitable as a gas supply for the first source of analyte gas 9), and alternative arrangements for providing a peak or pulsed supply of analyte gas, representing the second source or analyte gas 11. Analyte gas supplies of the first type are shown in FIGS. 18 to 25; analyte gas supplies of the second type are shown in FIGS. 26 to 29.

For the provision of a continuous flow of gas from the first source of analyte gas 9, a vial 18 may be used. There a number of techniques by which analyte can be generated inside the gas phase of the vial 18. For example, a gaseous sample may be collected inside the closed volume of a vial 18, either because the analyte molecules are already in gaseous form, or by the reaction of the first gaseous molecule with another gaseous molecule either in the closed volume of the vial 18 or in a separate (subsequent) reaction cell. For example, hydrocarbon maybe decomposed into $CO_2$ in the reaction cell.

Alternatively, the gaseous analyte may be provided through equilibration between a solid or liquid phase and a gaseous head space in the vial 18. This equilibration can be supported, for example, through heat, radiation, mechanical movement and so forth. Still further, a gaseous analyte gas supply may be generated through a chemical reaction of a solid or liquid with an added reagent and/or heat radiation, catalysis and so forth.

Figure 19:
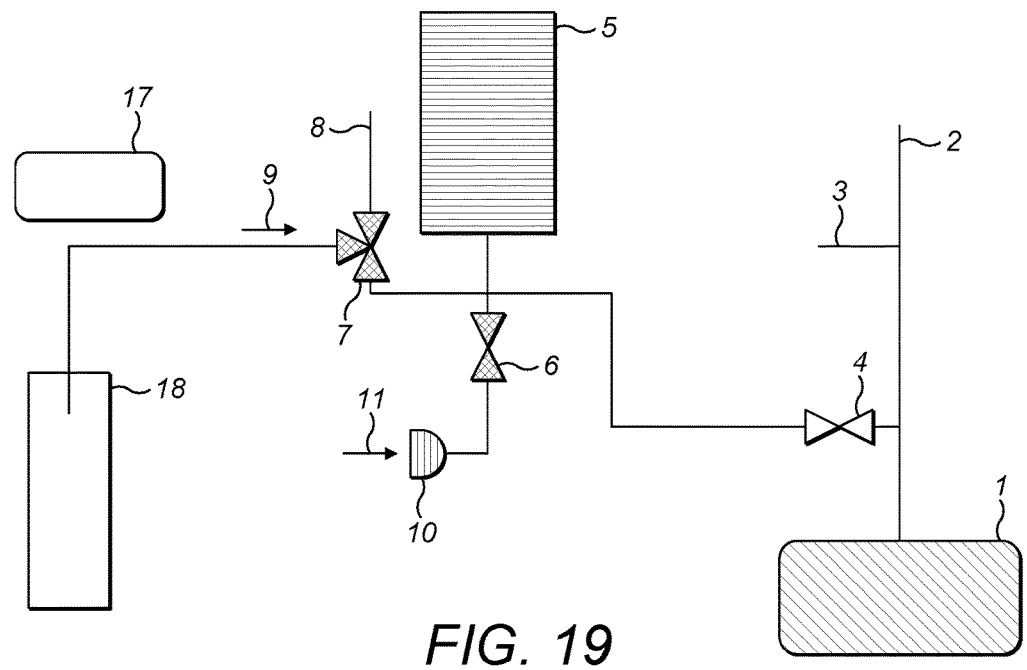
FIG. 19 shows the gas inlet supply of FIG. 2, together with a first arrangement for supply of a first analyte gas.

FIG. 19 shows the gas inlet system of FIG. 2, together with a first arrangement for the supply of analyte gas, in the form of a vial 18. A sample (not shown in FIG. 19), which may be generated in, for example, any of the ways described above, resides in the head space of the vial 18. In the embodiment of FIG. 19, transfer of the sample to the first supply valve 7 as the first source of analyte gas 9 is done by vacuum.

A syringe, (again not shown in FIG. 19) is injected into the sample vial 18 through a septum. The other end of the syringe is connected through a gas supply line to the first supply valve 7. Injection of the syringe into the sample vial 18 through the septum can be done manually, or by the use of an auto-sampler 17.

A vacuum is generated by opening the variable volume reservoir 5 so as to expand the volume thereof. This causes the gaseous sample within the vial 18 to be sucked along the gas supply line, into the first supply valve 7.

Because the pressure difference generates a significant flow rate, particularly upon commencement, diffusion processes are negligible. Two options then present. Firstly, if the quantity is small, it may be advantageous to transfer most or all of it into the analyzer 1. In that case it is important that the volume of the variable volume reservoir 5 is substantially larger than the volume of the vial 18. If the volume of the vial 18 is, for example, 12 ml and the volume of the variable volume reservoir 5 is 100 ml, following transfer, 89% of the sample would be in the variable volume reservoir 5 and the resultant pressure would be 107 mbar.

Where the sample quantity is greater, a large sample container permits only a small proportion of the sample to be removed from it. In that case, the pressure in the sample container is only slightly affected.

Figure 20:
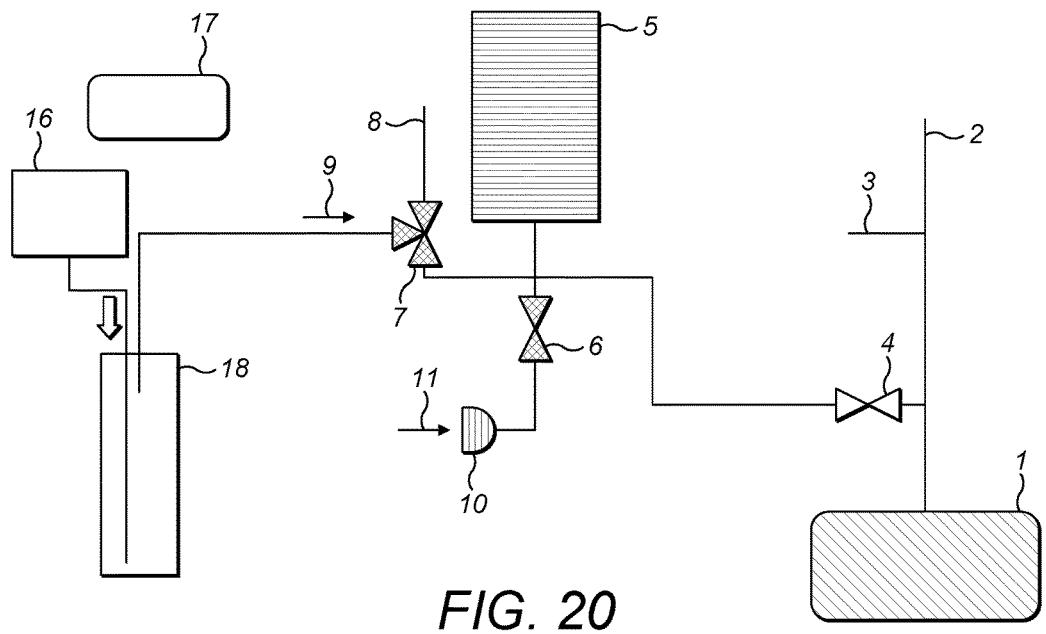
FIG. 20 shows the gas inlet supply of FIG. 2 together with a second arrangement for supply of a first analyte gas.

FIG. 20 shows the arrangement of FIG. 2, together with a second arrangement for supply of analyte gas. In this embodiment, the transfer is of analyte to the gas inlet system is achieved through flushing. In FIG. 20, a vial 18 is once again provided. A double needle (consisting of two concentric tubes), or alternatively two single needles, are injected into the sample vial 18 through a septum. Again, injection may be done manually or through the use of an auto sampler 17. Sample transfer from the vial 18 is commenced through the setting of a constant carrier gas flow from an mfc or similar device 16, to one exit of the double needle or to one of the two single needles. It is advantageous to lead the flow of carrier gas into the vial 18 to the bottom of the vial 18, whilst the exit is at the top of the vial 18. By doing this, the probability of blocking the exit capillary by particles or fluids agglomerating at the bottom of the vial 18 is reduced.

Other than blowing of the analyte gas out of the exit towards the first supply valve 7 along a gas supply line, rather than sucking it along a gas supply line to that first supply valve 7, as in FIG. 19, the sample transfer and measurement is as otherwise described.

(i) Continuous Carrier Gas Flow with Peak or Pulse Analyte Gas in it

The embodiments described above in connection with FIGS. 19 and 20 provide a continuous flow of analyte gas entrained within a carrier gas. FIGS. 21 to 25 show some exemplary embodiments of analyte supplies that produce a peak or pulsed flow of analyte gas within a continuous flow of carrier gas.

As explained above, where the analyte gas flow is a gas pulse and is thus generally not constant in time, it does not have the same isotopic composition throughout the pulse. Thus it is desirable to ensure that the whole pulse is sampled, either through a transfer of the whole pulse into the variable volume reservoir 5, or by transferring only a part of the pulse, by splitting away part of the gas mixture, as described above, in Section I(ii), during the whole time of the analyte pulse.

Measurement then takes place in accordance with the description set out in I(iii) above.

In order to permit determination of when, in the carrier gas flow, the analyte gas pulse occurs—and hence, when measurement should be started—various techniques can be employed. For example, in some circumstances, the time of commencement of the pulse is already known. This is the case, for example, when an elemental analyzer is employed. It is known when the sample is placed within the elemental analyzer and the transfer time of the analyte through and out of the elemental analyzer is also known (and is a short period of time). Alternatively, where the time is not known, an additional detector such as a thermal conductivity detector (TCD) may be employed. Further, a technique similar to that described above in Section I(i)(b) above can be employed. In particular, with the gas inlet system 20 of FIG. 2 arranged in the configuration of FIG. 9, the analyzer 1 may be used to determine the concentration of the sample. As soon as the concentration rises, the variable volume reservoir 5 may start to expand. The disadvantage of this last technique is that, by definition, a part of the sample at the beginning of the peak or pulse cannot be sampled because there will be a finite reaction time between detecting the start of the rise in concentration and the commencement of increase in volume of the variable volume reservoir 5.

Figure 21:
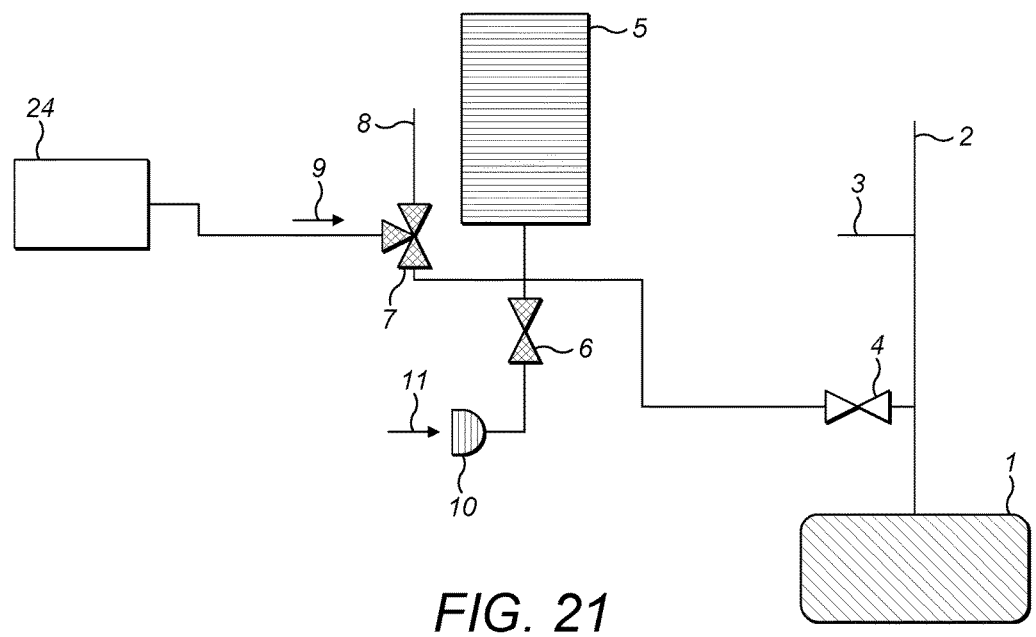
FIG. 21 shows the gas inlet supply of FIG. 2 together with a third arrangement for supply of a first analyte gas.

FIG. 21 shows an arrangement of the gas inlet system of FIG. 2 with an elemental or total organic carbon (TOC) analyzer 24 employed to provide the first source of analyte gas 9. Carrier gas is also supplied with the analyte gas from the elemental or TOC analyzer 24 and the nature of the carrier gas may differ depending upon the application.

Figure 22:
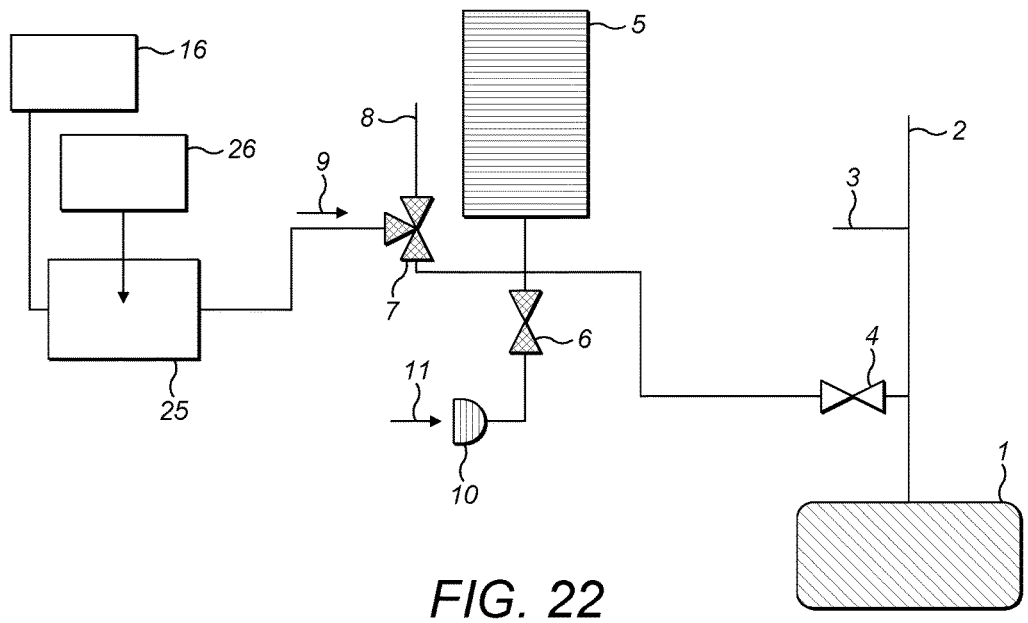
FIG. 22 shows the gas inlet supply of FIG. 2 together with a fourth arrangement for supply of a first analyte gas.

FIG. 22 shows an alternative arrangement for the provision of a first source of analyte gas 9. In FIG. 16, a closed laser chamber 25 is provided. Solid or liquid, and very occasionally gaseous samples are introduced into the closed laser chamber 25 and are evaporated or combusted via an energy source 26 such as a laser. Carrier gas is supplied to the closed laser chamber 25 from an mfc 16 so as to entrain the combusted or ablated sample to the first supply valve 7 along the carrier gas lines.

Figure 23:
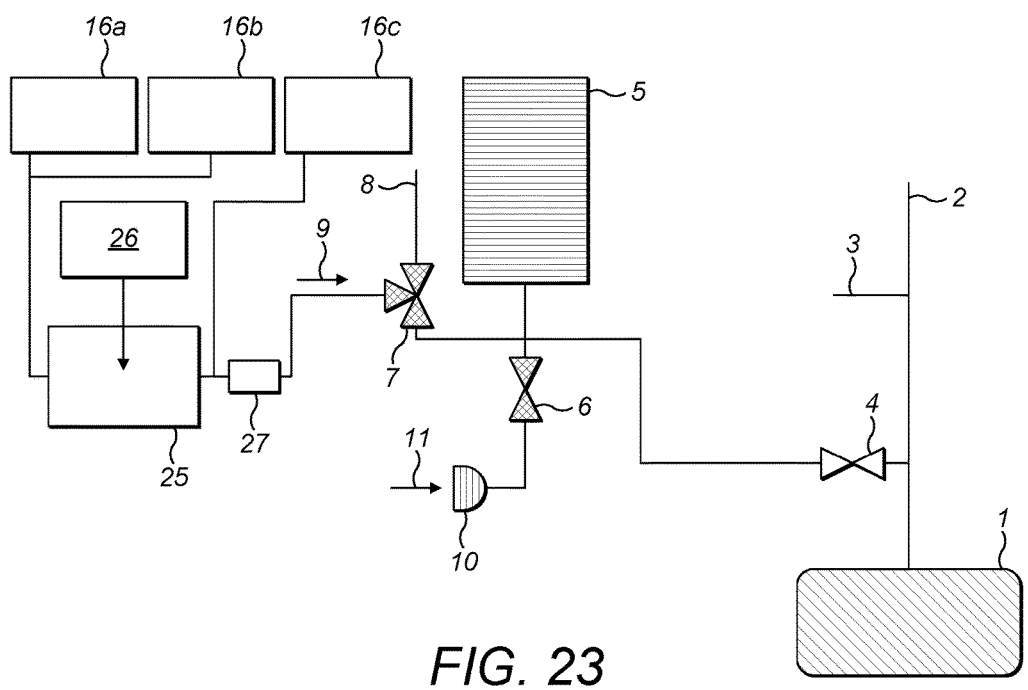
FIG. 23 shows the gas inlet supply of FIG. 2 together with a fifth arrangement for supply of a first analyte gas.

As an alternative to the arrangement of FIG. 22, additional carrier gas may be supplied through further mfcs 16b,16c as shown in FIG. 23. For many applications, it may also be useful to employ a post combustion reactor 27, in line between the closed laser chamber 25 and the first supply valve 7.

Figure 24:
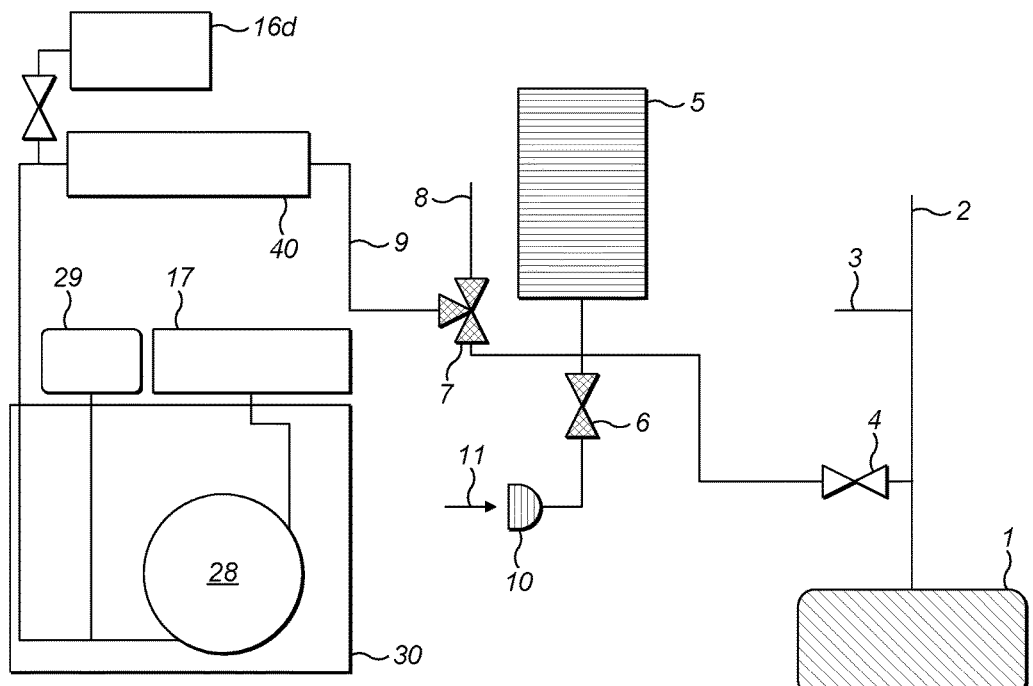
FIG. 24 shows the gas inlet supply of FIG. 2 together with a sixth arrangement for supply of a first analyte gas.

Still a further example of a pulsed analyte gas supply for the gas inlet system of FIG. 2 is shown in FIG. 24. The concept of converting a time varying analyte flow in a carrier gas flow, into a time constant, controllable analyte gas flow as described herein, and the advantage that the technique may permit transfer of up to 100% of the analyte into the analyzer 1, means that the gas inlet system in accordance with the present invention is ideally suited to gas chromatography (GC) applications. The drawback, however, particularly for embodiments of the present invention which employ a laser analyzer as the analyzer 1, is that such laser analyzers require sample amounts which are suited only to certain GC applications, for example preparative GC where larger sample volumes are encountered.

As seen in FIG. 24, an auto sampler 17 is employed to inject sample into a gas chromatograph 28. Downstream of the GC 28, the sample is oxidised using an oxidation reactor 40. Oxidation reactor 40 ideally comprises a metal oxide (for example, copper and/or nickel-oxide) which oxidise the sample gas. During this process, the metal oxide is reduced. Thus, it is necessary to re-oxidise it after a number of samples. This is achieved by applying oxygen or air from a suitable source 16d to the reactor 40. Alternatively, the oxidising gas flow may be continuous, even during oxidation of the sample. However, the former embodiment is preferred, because in this way the carrier gas composition is not modified by the oxidising gas (or, at least, only slightly modified). This can be particularly advantageous during analysis in the analyzer 1.

As a GC chromatogram consists of a number of peaks, it is necessary to isolate only interesting peaks by connecting the first source of analyte gas 9 to the variable volume reservoir 5, by appropriate switching of the first supply valve 7, and by commencing expansion of the variable volume reservoir 5. The time at which selection of an interesting peak takes place is determined through the use of an additional detector 29 such as a flame ionisation detector (FID). Part of the gas flow after the GC is split away through a split 30 to the FID detector 29. Alternatively, it may be possible to use an in line detector, located where the split 30 is shown in FIG. 24. Relatively few detector types are capable of this. One such suitable detector is a thermal conductivity detector (TCD).

There are several options to investigate several peaks within one gas chromatogram. Firstly, it may be accepted that only one peak per injection can be analyzed. Then the number of injections is increased to take that into account. Secondly, instead of a single variable volume reservoir 5, multiple reservoirs may be employed, each of which individually stores separate peaks. Still further, a stopped flow approach may be employed in the GC. After a first peak is stored in the variable volume reservoir 5, and whilst it is being processed, the carrier gas flows in the gas chromatograph 28 so that the other peaks are "parked" in that GC 28. The stopped flow approach, though rarely employed in practice, is known in the art—see for example Analytical Chemistry 2008, Volume 80, Pages 5481-5486 which describes a GC/NMR coupling. Peaks may be broadened through a diffusion process—see for example Chromatographia 14(12), 1981, 695-696. There are, however, columns where these effects are negligible: see, for example, (http://www.sigmaaldrich.com/content/dam/sigma-aldrich/countries/japan/analytical-chromatography/doc/j-t412094.pdf)

Figure 25:
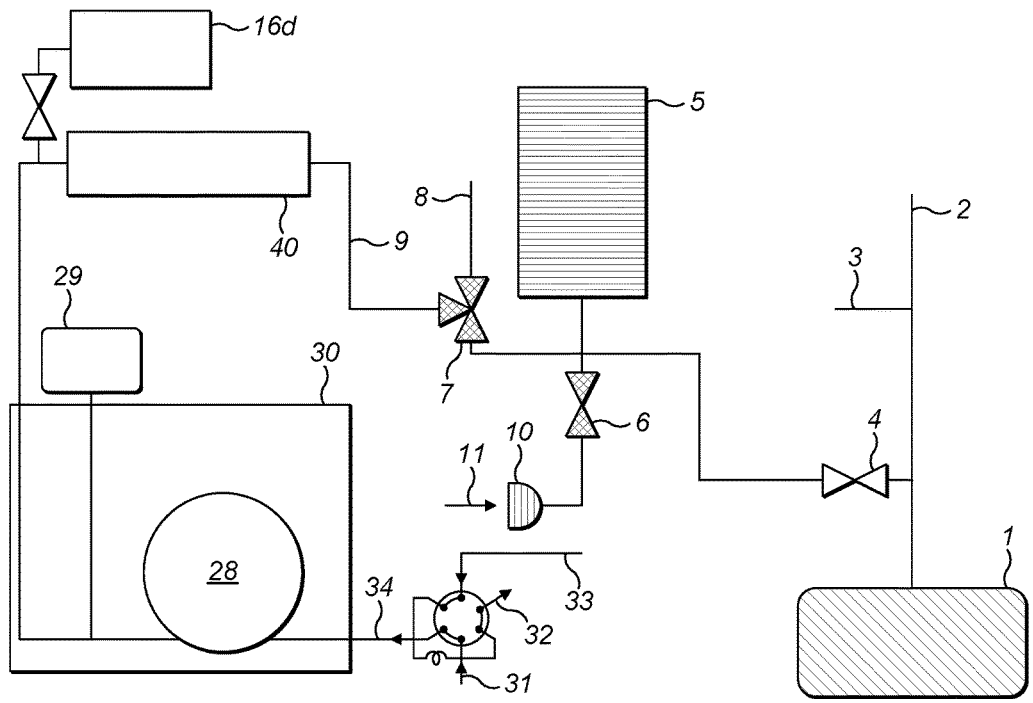
FIG. 25 shows the gas inlet supply of FIG. 2 together with a seventh arrangement for supply of a first analyte gas.

As still another option within the gas inlet system having a GC input coupling is to employ an injection loop valve. This is shown in FIG. 25, which is similar to the arrangement of FIG. 24, save for the inclusion of an injection loop valve 35. In the arrangement of FIG. 25, a constant gas flow, for example, a mixture of hydrocarbons sourced naturally or from a landfill, is supplied from a source 33 to the injection loop valve 35. The gas from the source 33 passes through a loop 34 in the injection loop valve 35 and is stored there. When the injection loop valve 35 is switched, carrier gas flow is injected from carrier gas supply 31 into the injection loop valve 35 and then transfers the stored gas into the gas chromatograph 28. 32 is a vent line without a valve.

(ii) Uses of the Discrete Sampling Inlet Port 10 with a Second Source of Analyte Gas 11

Figure 26:
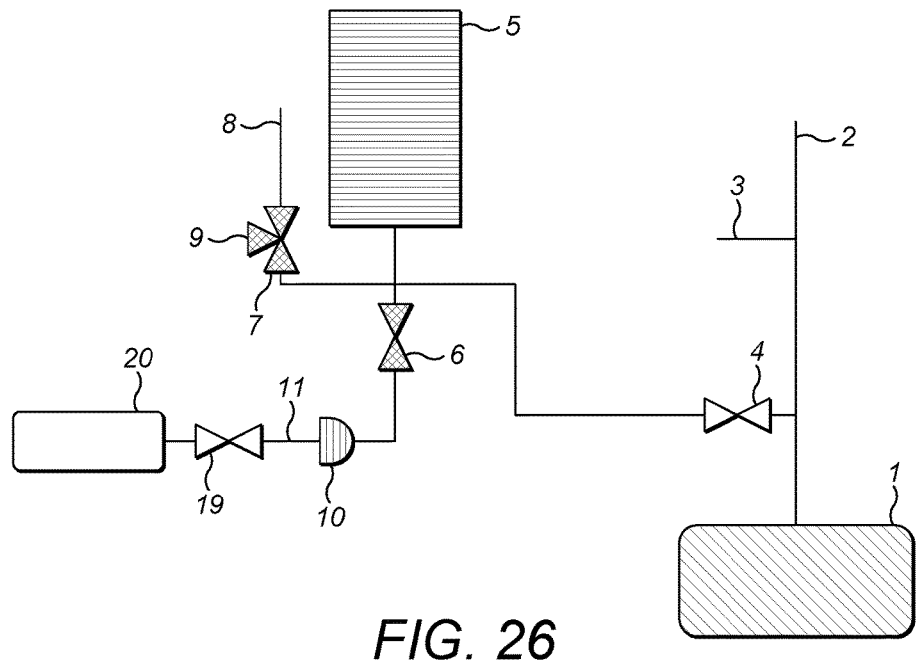
FIG. 26 shows the gas inlet supply of FIG. 2 together with a first arrangement for a second analyte gas supply.

FIG. 26 shows a first embodiment for the provision of a second source of analyte gas 11 to the gas inlet system 20 of FIG. 2. The port 10 preferably employs a (fingertight) screw thread connector, although a Cajon port may be used instead. To the port 10 is connected a gas sampling tube or bag 20. The measurement of sampling bag 20 using analyzer 1 is in accordance with Section II(iii) above. Between flushing of the various gas supply lines in the gas supply system 20 (Section II(iv)) and measurement (Section II(iii)), a manual valve 19 between the sampling tube or bag 20, and the port 10, is opened by a user.

Figure 27:
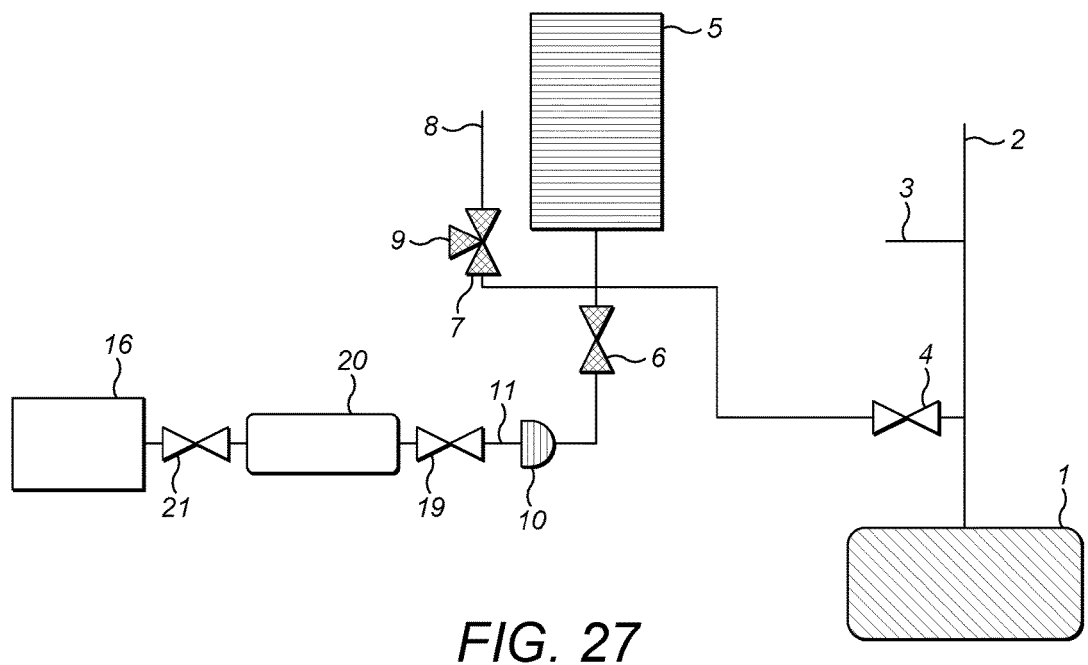
FIG. 27 shows the gas inlet supply of FIG. 2 together with a second arrangement for a second analyte gas supply.

In a variant of the implementation of FIG. 26, the sampling tube or bag 20 is not evacuated by the creation of a vacuum within the variable volume reservoir 5, but is instead flushed out using carrier gas from an mfc or similar by direct analogy with FIGS. 19 and 20 above. A suitable arrangement is shown in FIG. 27. The sample preparation, supply, capture in the variable volume reservoir 5 and subsequent analysis is as previously described, save that it is necessary for the user to open manual valves 25 and 27, and save that the mfc 16 should be set to a specified value at the start of measurement.

Figure 28:
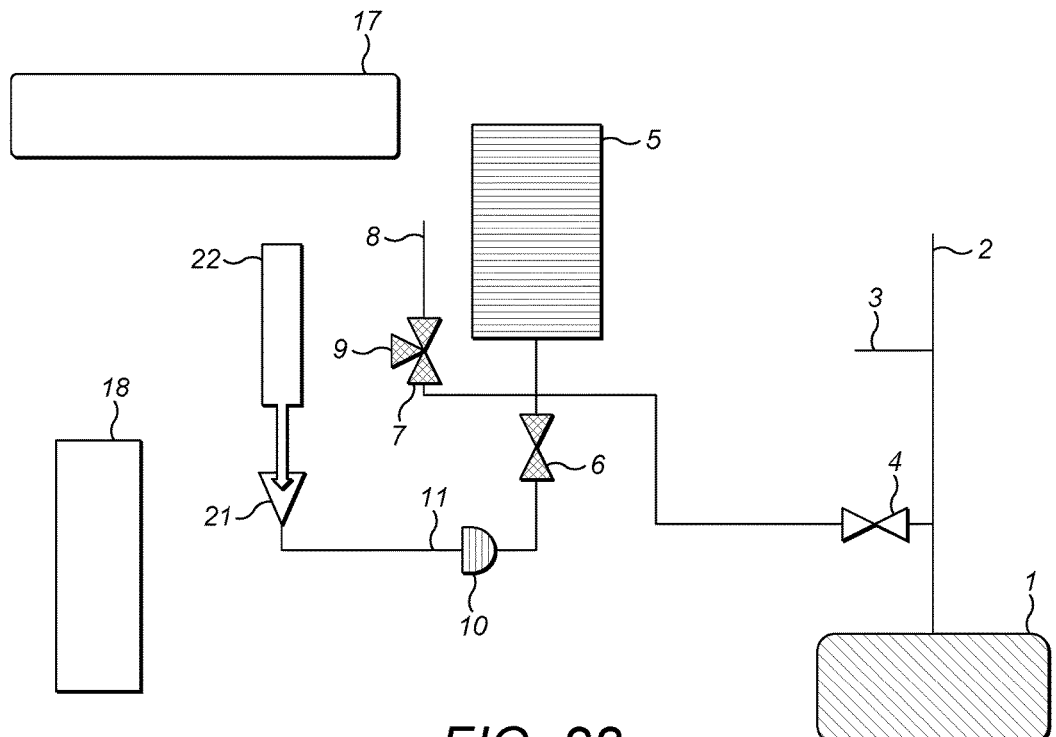
FIG. 28 shows the gas inlet supply of FIG. 2 together with a third arrangement for a second analyte gas supply.

FIG. 28 shows still a further possible arrangement for the provision of a discrete sample to the port 10. In FIG. 28, a septum port 21 is connected to the port 10. After flushing a supply line in accordance with Section II(iv) above, the gas filled syringe 22 is injected into the septum. This can be done manually or through the use of an auto sampler 17. Gas from the syringe may be taken from a vial device 18. Such an arrangement is advantageous where there is a continuous reaction in a larger vial 18, and the goal is to monitor this reaction several times after timed intervals.

Figure 29:
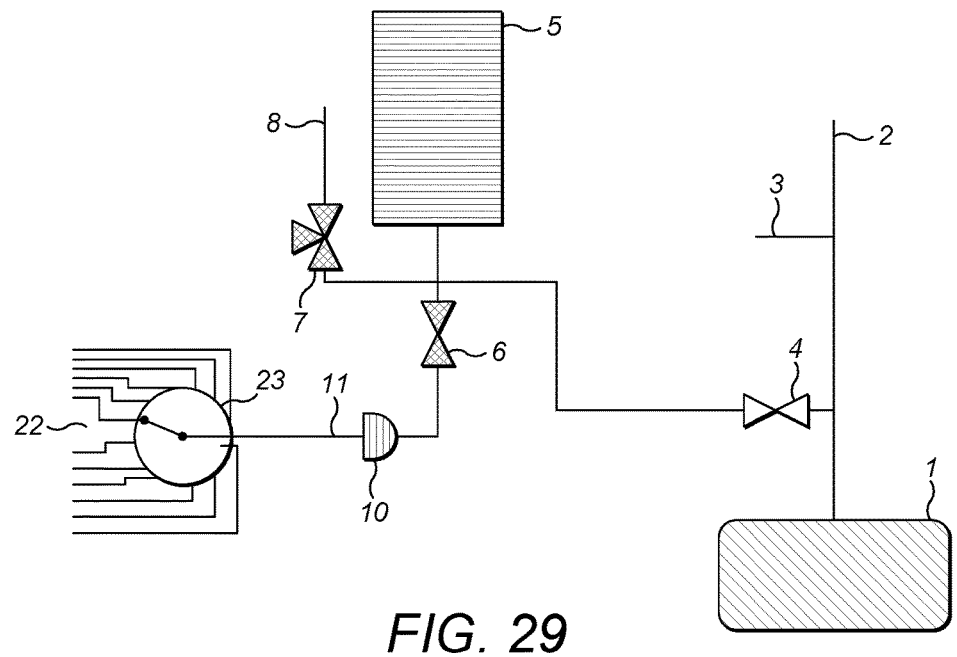
FIG. 29 shows the gas inlet supply of FIG. 2 together with a fourth arrangement for a second analyte gas supply.

Although the foregoing describes various discrete sample injection arrangements as a second source of analyte gas 11, any of these arrangements alone or in combination may be combined using a multi-port device. A suitable arrangement is shown in FIG. 29. Here, a multi-port 22 is connected to the port 10 so that the total number of ports available for injection of analyte is extended by a factor n (where n is the number of inlets to the multi-port 22). The ports of the multi-port may themselves be provided with screw thread connectors or Cajon ports so as to allow rapid connection and disconnection of multiple sample supply arrangements to the different inlet ports of the multi-port 22. Internally, the multi-port may be constructed of a number of 2/2 or 3/2 way valves, but most preferably, the multi-port contains a multi-position selection valve 23.

Before commencing measurement, each separate port of multi-port 22 may be flushed according to the procedure set out above in connection with FIG. 26, 27 or 28. As soon as a first port of the multi-port 22 has successfully been flushed, the multi-port 22 may then be switched to a next position for subsequent flushing.

Although a number of embodiments have been described, the skilled reader will readily recognize that various alternative arrangements may be contemplated. Moreover, it is to be understood, in the foregoing, that the terms "first source of analyte gas" and "second source of analyte gas" are not intended to imply necessarily that the analyte gases themselves are different. As has been explained, the first source of analyte gas is, in the embodiments described, either a continuous or pulsed flow of analyte gas within a continuous flow of carrier gas, whilst the second source of analyte gas is exemplified as a discrete sampling arrangement. However, the terms "first" and "second", as used in the claims in respect of the analyte gas sources, are not intended to imply one or other of the analyte supply types (continuous, pulsed, discrete . . . ), but are simply used as terms to distinguish between alternative analyte gas supplies that maybe present.

The gas inlet system preferentially comprises a variable volume reservoir, as described. However, the reservoir does not necessarily need to be of variable volume for the gas inlet to function. The gas analyte can be taken up and/or expelled from a reservoir of fixed volume, for example by control of the gas flow into a (fixed volume) reservoir and/or through the use of one or more pumps. Furthermore, the volume of the reservoir may be fixed during take up of the analyte, but then compressed to expel it, or of variable volume during uptake of the analyte gas, but of fixed volume when subsequently expelled.

The foregoing description and accompanying drawings illustrate that in various embodiments the invention has the following capabilities:

To take up a sample (analyte) gas by increasing the volume of the variable volume reservoir 5;

To mix a sample gas thoroughly during this uptake, e.g. with a carrier gas;

To take up a complete sample amount;

To take up only a part of a sample amount (in that case to potentially use the remainder of the sample to determine the sample concentration);

To dilute a sample inside the variable volume reservoir 5 by pumping carrier gas into the variable volume reservoir 5;

To determine an analyte gas concentration by using a portion of a stored gas volume;

To use the variable volume reservoir 5 to generate a pressure slightly above ambient (atmospheric) pressure in order to drive a (diluted) sample gas flow of an known amount, in order to:
  Generate a defined, constant or non-constant, sample flow;
  Dilute this defined sample flow using an open split device with a carrier gas, connected to a spectrometer which admits a defined gas amount;
  Generate and control a flow with a constant concentration of the analyte gas into the spectrometer, and to match the size of the flow to the analytical application, which can extend greatly the dynamic range of the analyser and/or overcome linearity problems;
  Convert a non-constant concentration in a gas flow into a constant concentration gas flow;

To use the variable volume reservoir 5 to generate a pressure slightly lower than ambient pressure (i.e. a slight vacuum) in order to suck in analyte which is at ambient pressure and either kept at ambient pressure or in a container of a very large volume;

To use the variable volume reservoir 5 to generate a pressure considerably lower than ambient pressure (up to 0 bar) in order to suck in sample e.g. from a sampling container with a fixed, limited volume;

To use the variable volume reservoir 5 to generate an over- and under-pressure and, in connection with an open split device with a carrier gas supplied to the gas inlet system, to flush a portion of the gas inlet system, e.g. with zero air, and to actively pump away impurities;

To use a force at the variable volume reservoir 5 or a pressure at a part of the variable volume reservoir 5 that is not in contact with the analyte gas in order to determine the pressure within the variable volume reservoir 5.

What is claimed is:

1. A method of coupling an analyte gas to an isotope ratio spectrometer, comprising:
    supplying a first analyte gas to a variable volume reservoir of a gas inlet system;
    expanding the variable volume reservoir so as to take up the first analyte gas into the reservoir;
expelling, by compressing the variable volume reservoir, the first analyte gas, or a first analyte mixture containing the first analyte gas, from the reservoir at a controlled flow rate, by controllably adjusting the volume inside the variable volume reservoir at a predetermined rate;
    directing a flow of the said first analyte gas or first analyte mixture to the spectrometer at the controlled flow rate; and
    selectively supplying a carrier gas to the spectrometer and/or to the variable volume reservoir;
    wherein the reservoir is expanded at a rate faster than the rate of supply of the first analyte gas so as to create a vacuum within the reservoir and thereby to suck in substantially all of the first analyte gas supplied by a first analyte gas supply during a sample uptake period wherein a part of the carrier gas passes to the variable volume reservoir so as to dilute the concentration of the first analyte gas in the reservoir.

2. The method of claim 1, wherein at least a part of the carrier gas passes to an open split located upstream of the spectrometer and/or the variable volume reservoir.

3. A method of coupling an analyte gas to an isotope ratio spectrometer, comprising:
    supplying a first analyte gas to a variable volume reservoir of a gas inlet system;
    expanding the variable volume reservoir so as to take up the first analyte gas into the reservoir;
    expelling, by compressing the variable volume reservoir, the first analyte gas, or a first analyte mixture containing the first analyte gas, from the reservoir at a controlled flow rate, by controllably adjusting the volume inside the variable volume reservoir at a predetermined rate;
    directing a flow of the said first analyte gas or first analyte mixture to the spectrometer at the controlled flow rate, wherein at least a part of the carrier gas passes to an open split located upstream of the spectrometer and/or the variable volume reservoir;
    diluting the first analyte gas once the variable volume reservoir has taken it up by:
    isolating the variable volume reservoir from a supply of the first analyte gas;
    compressing the reservoir by a known amount so as to expel a proportion of the first analyte gas to the spectrometer and to expel the remaining portion of the first analyte gas to the open split;
    subsequently expanding again the variable volume reservoir to or by a predetermined amount, at a speed which is smaller than the difference between the uptake of the spectrometer and the carrier gas flow, so as to cause carrier gas to be drawn into the variable volume reservoir and to dilute the first analyte gas therein;
    wherein the predetermined amount of expansion of the reservoir is selected on the basis of the subsequently desired dilution/concentration of the first analyte gas.

4. A method of coupling an analyte gas to an isotope ratio spectrometer, comprising:
    supplying a first analyte gas to a variable volume reservoir of a gas inlet system;
    expanding the variable volume reservoir so as to take up the first analyte gas into the reservoir;
    expelling, by compressing the variable volume reservoir, the first analyte gas, or a first analyte mixture containing the first analyte gas, from the reservoir at a controlled flow rate, by controllably adjusting the volume inside the variable volume reservoir at a predetermined rate;
directing a flow of the said first analyte gas or first analyte mixture to the spectrometer at the controlled flow rate, wherein at least a part of the carrier gas passes to an open split located upstream of the spectrometer and/or the variable volume reservoir;
    wherein the reservoir is expanded at a rate slower than the rate of supply of the first analyte gas so as to create a vacuum within the reservoir and thereby to suck a part, but not all, of the first analyte gas being supplied by a first analyte gas supply during a sample uptake period.

5. The method of claim 4, further comprising determining the first analyte gas concentration within the variable volume reservoir when the first analyte gas concentration is present therein.

6. The method of claim 1, comprising determining the concentration of the first analyte gas within the variable volume reservoir by:
    connecting the variable volume reservoir to an opening once the first analyte gas has been taken up into the reservoir;

decreasing the volume of the reservoir to a known amount by expelling a part of the contents of the reservoir to the opening; and determining the concentration of the first analyte gas using the spectrometer.

7. The method of claim 1, further comprising:

isolating the variable volume reservoir from the spectrometer and from a supply of the first analyte gas, once the reservoir has taken up first analyte gas through expansion of the reservoir;

compressing the volume of the reservoir following the said isolation of the reservoir, until the pressure of the gas within the reservoir reaches a chosen pressure; and connecting the variable volume reservoir to the spectrometer for expulsion of at least a part of the contents of the reservoir thereto.

8. The method of claim 1, further comprising:

determining an optimum equilibrium flow into the spectrometer.

9. The method of claim 4, wherein at least a portion of the first analyte gas not sucked into the variable volume reservoir is sucked into the spectrometer.

10. The method of claim 4, wherein the open split receives a flow of first analyte gas from the first analyte gas supply in excess of the sum of the input flow rate of the first analyte gas into the variable volume reservoir and the input flow rate of the laser analyzer.

11. The method of claim 4, further comprising determining the first analyte gas concentration within the variable volume reservoir when the first analyte gas concentration is present therein.

12. The method of claim 11, wherein the step of determining the first analyte gas concentration comprises calculating the concentration based upon measurement or inference of flow rates and volumes within the gas inlet system.

13. The method of claim 11, wherein the step of determining the first analyte gas concentration comprises inferring the concentration of the gas within the reservoir based upon the concentration of the first analyte gas which does not enter the variable volume reservoir as it is expanded.

14. The method of claim 1, comprising determining the concentration of the first analyte gas within the variable volume reservoir by:

connecting the variable volume reservoir to an opening once the first analyte gas has been taken up into the reservoir;

decreasing the volume of the reservoir to a known amount by expelling a part of the contents of the reservoir to the opening; and determining the concentration of the first analyte gas using the spectrometer.

15. The method of claim 14, wherein the opening is a second open split, the method further comprising:

isolating the variable volume reservoir from the spectrometer whist the volume of the reservoir is being decreased to the known amount, and connecting the variable volume reservoir to the spectrometer subsequently.

16. The method of claim 1, further comprising:

isolating the variable volume reservoir from the spectrometer and from a supply of the first analyte gas, once the reservoir has taken up first analyte gas through expansion of the reservoir;

compressing the volume of the reservoir following the said isolation of the reservoir, until the pressure of the gas within the reservoir reaches a chosen pressure; and connecting the variable volume reservoir to the spectrometer for expulsion of at least a part of the contents of the reservoir thereto.

17. The method of claim 1, further comprising:

supplying the first analyte gas to the variable volume reservoir as a series of gas pulses.

18. The method of claim 17, further comprising:

capturing substantially all of the first analyte gas in one or more gas pulses arriving at the reservoir.

19. The method of claim 17, further comprising:

capturing only a part of the first analyte gas in one or more gas pulses arriving at the reservoir.

20. The method of claim 1, further comprising:

storing a sample in a sample holder, forcing the sample out of the sample holder by flushing carrier gas into the sample holder, so as to generate the said first analyte gas, entrained with carrier gas, for supply to the variable volume reservoir.

21. The method of claim 1, comprising injecting a sample into a gas chromatograph; and oxidizing the sample gas eluted from the gas chromatograph, so as to produce a supply of the first analyte gas.

22. The method of claim 1, further comprising flushing the gas inlet system with a carrier gas by:

(a) isolating the variable volume reservoir from a supply of first analyte gas;

(b) connecting the reservoir to a carrier gas supply line that selectively supplies carrier gas from a carrier gas supply to the spectrometer;

(c) expelling the contents of the reservoir to the carrier gas supply line by compression of the reservoir; and (d) expanding the reservoir with the first analyte gas supply still isolated, so as to draw carrier gas from the carrier gas supply line into the reservoir.

* * * * *